US012275984B2

(12) United States Patent
Bava

(10) Patent No.: US 12,275,984 B2
(45) Date of Patent: Apr. 15, 2025

(54) SEQUENTIAL HYBRIDIZATION AND QUENCHING

(71) Applicant: 10x Genomics, Inc., Pleasanton, CA (US)

(72) Inventor: Felice Alessio Bava, Rome (IT)

(73) Assignee: 10X GENOMICS, INC., Pleasanton, CA (US)

( * ) Notice: Subject to any disclaimer, the term of this patent is extended or adjusted under 35 U.S.C. 154(b) by 559 days.

(21) Appl. No.: 17/683,856

(22) Filed: Mar. 1, 2022

(65) Prior Publication Data

US 2022/0282306 A1    Sep. 8, 2022

Related U.S. Application Data

(60) Provisional application No. 63/155,684, filed on Mar. 2, 2021.

(51) Int. Cl.
*C12Q 1/6816*    (2018.01)

(52) U.S. Cl.
CPC .................................. *C12Q 1/6816* (2013.01)

(58) Field of Classification Search
CPC ............ C12Q 1/6816; C12Q 2525/155; C12Q 2537/143; C12Q 2525/161; C12Q 2565/101
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,512,462 A | 4/1996 | Cheng | |
| 5,635,352 A | 6/1997 | Urdea et al. | |
| 5,695,940 A | 12/1997 | Drmanac et al. | |
| 6,054,274 A | 4/2000 | Sampson et al. | |
| 6,265,552 B1 | 7/2001 | Schatz | |
| 6,291,187 B1 | 9/2001 | Kingsmore et al. | |
| 6,306,597 B1 | 10/2001 | Macevicz | |
| 6,323,009 B1 | 11/2001 | Lasken et al. | |
| 6,344,329 B1 | 2/2002 | Lizardi et al. | |
| 6,368,801 B1 | 4/2002 | Faruqi | |
| 6,391,937 B1 | 5/2002 | Beuhler et al. | |
| 6,534,266 B1 | 3/2003 | Singer | |
| 7,019,129 B1 | 3/2006 | Cook et al. | |
| 7,255,994 B2 | 8/2007 | Lao | |
| 7,264,929 B2 | 9/2007 | Rothberg et al. | |
| 7,345,159 B2 | 3/2008 | Ju et al. | |
| 7,473,767 B2 | 1/2009 | Dimitrov | |
| 7,534,991 B2 | 5/2009 | Miller et al. | |
| 7,544,794 B1 | 6/2009 | Benner | |
| 7,555,155 B2 | 6/2009 | Levenson et al. | |
| 7,566,537 B2 | 7/2009 | Balasubramanian et al. | |
| 7,632,641 B2 | 12/2009 | Dirks et al. | |
| 7,655,898 B2 | 2/2010 | Miller | |
| 7,709,198 B2 | 5/2010 | Luo et al. | |
| 7,879,986 B2 | 2/2011 | Berry et al. | |
| 7,893,227 B2 | 2/2011 | Wu et al. | |
| 7,910,304 B2 | 3/2011 | Drmanac | |
| 7,914,987 B2 | 3/2011 | Fredriksson et al. | |
| 7,941,279 B2 | 5/2011 | Hwang et al. | |
| 7,989,166 B2 | 8/2011 | Koch et al. | |
| 8,124,751 B2 | 2/2012 | Pierce et al. | |
| 8,199,999 B2 | 6/2012 | Hoyt et al. | |
| 8,268,554 B2 | 9/2012 | Schallmeiner | |
| 8,330,087 B2 | 12/2012 | Domenicali | |
| 8,415,102 B2 | 4/2013 | Geiss et al. | |
| 8,431,691 B2 | 4/2013 | McKernan et al. | |
| 8,460,865 B2 | 6/2013 | Chee et al. | |
| 8,462,981 B2 | 6/2013 | Determan et al. | |
| 8,481,258 B2 | 7/2013 | Church et al. | |
| 8,519,115 B2 | 8/2013 | Webster et al. | |
| 8,551,710 B2 | 10/2013 | Bernitz et al. | |
| 8,580,504 B2 | 11/2013 | Fredriksson et al. | |
| 8,604,182 B2 | 12/2013 | Luo et al. | |

(Continued)

FOREIGN PATENT DOCUMENTS

| | | |
|---|---|---|
| WO | WO 2011/112634 | 9/2011 |
| WO | WO 2017/079406 | 5/2017 |

(Continued)

OTHER PUBLICATIONS

Bingham et al. "Spatial-Omics: Novel Approaches to Probe Cell Heterogeneity and Extracellular Matrix Biology." Matrix biology 91-92 (2020): 152-166. (Year: 2020).*
Moffitt et al. "High-Throughput Single-Cell Gene-Expression Profiling with Multiplexed Error-Robust Fluorescence in Situ Hybridization." PNAS 113.39 (2016): 11046-11051. (Year: 2016).*
Juskowiak. "Nucleic Acid-Based Fluorescent Probes and Their Analytical Potential." Analytical & bioanalytical chemistry (Print) 399.9 (2011): 3157-3176. (Year: 2011).*
Chen et al., "Efficient in situ barcode sequencing using padlock probe-based BaristaSeq," Nucleic Acids Res. (2018) 46(4): e22.
Sun et al., "Integrating barcoded neuroanatomy with spatial transcriptional profiling enables identification of gene correlates of projections," Nat Neurosci. (2021) 24(6):873-885.

(Continued)

*Primary Examiner* — Cynthia B Wilder
*Assistant Examiner* — Amy M. Chattin
(74) *Attorney, Agent, or Firm* — MORRISON & FOERSTER LLP

(57) ABSTRACT

The present disclosure provides methods for detecting a nucleic acid molecule involving the use of a signal code sequence which corresponds to said nucleic acid molecule, comprising sequential hybridization of detectably labeled probes to allow detection of a signal code sequence. In particular, the present disclosure provides a method of sequential decoding comprising hybridization-directed quenching of detectable moieties that have already been imaged, allowing the newly added probe to be detected without the need to remove the previously imaged detectable moiety, thus providing an approach that reduces or eliminates the need for damaging probe stripping.

20 Claims, 6 Drawing Sheets

(56) References Cited

U.S. PATENT DOCUMENTS

| | | |
|---|---|---|
| 8,632,975 B2 | 1/2014 | Vander Horn et al. |
| 8,658,361 B2 | 2/2014 | Wu et al. |
| 8,771,950 B2 | 7/2014 | Church et al. |
| 8,951,726 B2 | 2/2015 | Luo et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,450,599 B2 | 10/2019 | Pierce et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2003/0013091 A1 | 1/2003 | Dimitrov |
| 2007/0166708 A1 | 7/2007 | Dimitrov et al. |
| 2010/0015607 A1 | 1/2010 | Geiss et al. |
| 2010/0047924 A1 | 2/2010 | Webster et al. |
| 2010/0055733 A1 | 3/2010 | Lutolf et al. |
| 2010/0112710 A1 | 5/2010 | Geiss et al. |
| 2010/0261026 A1 | 10/2010 | Ferree et al. |
| 2010/0262374 A1 | 10/2010 | Hwang et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2014/0194311 A1 | 7/2014 | Gullberg et al. |
| 2014/0371088 A1 | 12/2014 | Webster |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Deisseroth et al. |
| 2017/0220733 A1 | 8/2017 | Zhuang et al. |
| 2017/0253918 A1 | 9/2017 | Kohman |
| 2018/0051322 A1 | 2/2018 | Church et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0106733 A1 | 4/2019 | Kishi et al. |
| 2019/0112599 A1 | 4/2019 | Church et al. |
| 2019/0119735 A1 | 4/2019 | Deisseroth et al. |
| 2019/0144932 A1 | 5/2019 | Guo |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0164039 A1 | 6/2021 | Wang et al. |
| 2021/0238662 A1 | 8/2021 | Bava et al. |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1* | 11/2021 | Daugharthy ......... C12Q 1/6809 |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |

(56) References Cited

U.S. PATENT DOCUMENTS

| | | |
|---|---|---|
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Neuta et al. |
| 2023/0031996 A1 | 2/2023 | Neuta et al. |
| 2023/0035685 A1 | 2/2023 | Neuta et al. |
| 2023/0037182 A1 | 2/2023 | Bava et al. |
| 2023/0039148 A1 | 2/2023 | Verheyen |
| 2023/0041485 A1 | 2/2023 | Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schnall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen et al. |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | |
|---|---|---|
| WO | WO 2017/143155 | 8/2017 |
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/167526 | 8/2021 |
| WO | WO 2021/168326 | 8/2021 |
| WO | WO 2023/108139 | 6/2023 |
| WO | WO 2023/141476 | 7/2023 |
| WO | WO 2023/172915 | 9/2023 |
| WO | WO 2023/192302 | 10/2023 |
| WO | WO 2024/148300 | 7/2024 |

OTHER PUBLICATIONS

Archer et al., "Selective and flexible depletion of problematic sequences from RNA-seq libraries at the cDNA stage," BMC Genomics. (2014) 15(1):401.

Baner et al., "Signal amplification of padlock probes by rolling circle replication," Nucleic Acids Res. (1998) 26(22):5073-5078.

Bolognesi et al., "Multiplex Staining by Sequential Immunostaining and Antibody Removal on Routine Tissue Sections," J. Histochem. Cytochem. (2017); 65(8): 431-444.

Chemeris et al., "Real-time hybridization chain reaction," Dokl Biochem Biophys. (2008) 419: 53-55.

Chen et al., "Nanoscale imaging of RNA with expansion microscopy," Nat Methods. (2016) 13:679-684.

Chen et al., "Expansion Microscopy," Science (2015) 347(6221):543-548.

Chen et al., "RNA imaging. Spatially resolved, highly multiplexed RNA profiling in single cells," Science. (2015) 348(6233): aaa6090. 16 pgs.

Choi et al., "Programmable in situ amplification for multiplexed imaging of mRNA expression," Nat Biotechnol. (2010) 28(11): 1208-1212.

Choi et al., "Third-generation in situ hybridization chain reaction: multiplexed, quantitative, sensitive, versatile, robust," Development. (2018) 6;145(12): dev165753.

Dean et al., "Rapid Amplification Of Plasmid And Phage DNA Using Phi29 DNA Polymerase And Multiply-Primed Rolling Circle Amplification," Genome Research (2001) 11:1095-1099.

Dirks et al., "Triggered amplification by hybridization chain reaction," Proc Natl Acad Sci U S A. (2004) 101(43): 15275-15278.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Forcucci et al., "All-plastic miniature fluorescence microscope for point-of-care readout of bead-based bioassays," J Biomed Opt. (2015) 20(10): 105010.

Frei et al., "Highly multiplexed simultaneous detection of RNAs and proteins in single cells," Nat Methods. (2016) 13(3): 269-275.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1): e7. doi: 10.1093/nar/gkn921.

Jamur et al., "Permeabilization of cell membranes," Method Mol. Biol. (2010) 588: 63-66 (abstract only).

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al. "Exponential amplification of recombinant-RNA hybridization probes." *Bio/technology* 6.10 (1988): 1197-1202.

(56) References Cited

OTHER PUBLICATIONS

McGinn et al., "New technologies for DNA analysis—a review of the READNA Project," N Biotechnol. (2016) 33(3): 311-30. doi: 10.1016/j.nbt.2015.10.003.
Mohsen et al., "The Discovery of Rolling Circle Amplification and Rolling Circle Transcription," Acc Chem Res. (2016) 49(11): 2540-2550.
Musumeci et al., "Fluorescence Sensing Using DNA Aptamers in Cancer Research and Clinical Diagnostics," Cancers (Basel). (2017) 9(12):174.
Nagendran et al., "Automated cell-type classification in intact tissues by single-cell molecular profiling," Elife. (2018) 7:e30510.
Nallur et al., "Signal amplification by rolling circle amplification on DNA microarrays," Nucleic Acids Res. (2001) 29(23): e118.
Niu et al., "Fluorescence detection for DNA using hybridization chain reaction with enzyme-amplification," Chem Commun (Camb). (2010) 46(18): 3089-91.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pirici et al., "Antibody elution method for multiple immunohistochemistry on primary antibodies raised in the same species and of the same subtype," J Histochem Cytochem. (2009) 57(6); 567-75.
Rajeswari et al., "Multiple pathogen biomarker detection using an encoded bead array in droplet PCR," J Microbiol Methods. (2017) 139: 22-28.
Rouhanifard et al. "ClampFISH detects individual nucleic acid molecules using click chemistry-based amplification," Nat Biotechnol. (2018) 17 pages. doi: 10.1038/nbt.4286.
Schweitzer et al., "Multiplexed protein profiling on microarrays by rolling-circle amplification," Nature Biotech. (2002) 20:359-365.
Schweitzer et al. "Immunoassays with rolling circle DNA amplification: A versatile platform for ultrasensitive antigen detection," Proc. Natl Acad. Sci. USA (2000) 97:10113-119.
Song et al., "Hybridization chain reaction-based aptameric system for the highly selective and sensitive detection of protein," Analyst. (2012) 137(6):1396-1401.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Tripathi et al., "Z Probe, An Efficient Tool for Characterizing Long Non-Coding RNA in FFPE Tissues," Noncoding RNA. (2018) 4(3):20.
Tsuneoka et al., "Modified in situ Hybridization Chain Reaction Using Short Hairpin DNAs," Front Mol Neurosci. (2020) 13:75.
Vandernoot et al., "cDNA normalization by hydroxyapatite chromatography to enrich transcriptome diversity in RNA-seq applications," Biotechniques, (2012) 53(6) 373-80.
Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.
Xia et al., "Recent advances in high-performance fluorescent and bioluminescent RNA imaging probes," Chem Soc Rev. (2017) 46(10):2824-2843.
Bibikova et al., "Quantitative gene expression profiling in formalin-fixed, paraffin-embedded tissues using universal bead arrays," Am J Pathol. Nov. 2004; 165(5):1799-807.
Capodieci et al., "Gene expression profiling in single cells within tissue," Nat Methods. (2005) 2(9): 663-5.
Conze et al., "Single molecule analysis of combinatorial splicing," Nucleic Acids Res. (2010) 38(16): e163.
Femino et al., "Visualization of single RNA transcripts in situ," Science. (1998) 280(5363): 585-90.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Gunderson et al. "Decoding randomly ordered DNA arrays." Genome research 14.5 (2004): 870-877.
Han et al., "Quantum-dot-tagged microbeads for multiplexed optical coding of biomolecules," Nat Biotechnol. (2001) 19(7): 631-5.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Maierhorfer et al., "Multicolor deconvolution microscopy of thick biological specimens," Am J Pathol. (2003) 162(2): 373-9.
Meade et al. "Multiplexed DNA detection using spectrally encoded porous SiO2 photonic crystal particles," Anal Chem. (2009) 81(7): 2618-25.
Raj et al., "Imaging individual mRNA molecules using multiple singly labeled probes," Nat Methods. (2008) 5(10): 877-879.
Sun et al., "Composite organic-inorganic nanoparticles as Raman labels for tissue analysis," Nano Lett. (2007) 7(2): 351-6.
Wählby et al., "Sequential immunofluorescence staining and image analysis for detection of large numbers of antigens in individual cell nuclei," Cytometry. (2002) 47(1): 32-41.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chem Int Ed Engl. (2006) 18;45(37): 6104-17.
Xiao et al., "Highly Multiplexed Single-Cell In Situ RNA and DNA Analysis by Consecutive Hybridization," Molecules. (2020) 25(21): 4900.
Zhao et al., "Advances of multiplex and high throughput biomolecular detection technologies based on encoding microparticles," Sci China Chem. (2011) 54(8):1185.

* cited by examiner

SEQUENTIAL HYBRIDIZATION AND QUENCHING

CROSS-REFERENCE TO RELATED APPLICATIONS

This application claims priority to U.S. Provisional Patent Application No. 63/155,684, filed Mar. 2, 2021, entitled "SEQUENTIAL HYBRIDIZATION AND QUENCHING," which is herein incorporated by reference in its entirety for all purposes.

FIELD

The present disclosure relates in some aspects to methods for analyzing the presence and/or localization of an analyte in a biological sample by sequential hybridization of oligonucleotide probes.

BACKGROUND

Nucleotide barcoding is used in a wide range of applications where it is desired to detect and differentiate multiple different analytes. Many barcoding methods use a limited pool of different detectable labels, and require multiple detection cycles in order to decode the barcode sequences. These methods typically involve repeatedly hybridizing a labelled detection probe, imaging the sample to detect the label that has been hybridized, and physically removing the hybridized labelled detection probe or detectable labels so that the next cycle can begin. In this way, a specified sequence of labels can be detected, forming a signal signature which distinguishes a particular analyte.

Removing the hybridized labelled detection probe often involves the use of high temperature and/or potentially toxic chemical agents such as formamide to denature or disrupt the hybridization between the barcode and the detection probe. However, these methods are particularly problematic for in situ assays since they can damage the sample and interfere with desired downstream reactions. Chemical or enzymatic cleavage of the fluorophores may also damage samples and typically requires a separate removal step, adding to the time required to perform the method. Thus, there is need for cost- and time-efficient methods which are suitable for high multiplicity in situ assays.

BRIEF SUMMARY

In some aspects, provided herein is a method for analyzing a biological sample, comprising: a) contacting a biological sample with a first probe, wherein: the first probe comprises a detectable moiety D1 and a hybridization sequence H1, the biological sample comprises a nucleic acid molecule comprising a hybridization sequence H1', and H1' hybridizes to H1; and b) contacting the biological sample with a second probe, wherein: the second probe comprises: (i) a hybridization sequence H2 that hybridizes to a hybridization region H2' of the nucleic acid molecule, the first probe, or a splint, (ii) a quencher Q1, and (iii) a detectable moiety D2, and Q1 quenches a detectable signal from D1, wherein a detectable signal from D2 is detected in the biological sample.

In some embodiments, D1 can remain in the biological sample during and/or after the contacting step b).

In any of the preceding embodiments, D1 can remain in the biological sample prior to, during, and/or after the detection of the detectable signal from D2.

In any of the preceding embodiments, D1 can remain in the first probe during and/or after the contacting step b).

In any of the preceding embodiments, D1 can remain in the first probe prior to, during, and/or after the detection of the detectable signal from D2.

In any of the preceding embodiments, the first probe remains hybridized to the nucleic acid molecule during and/or after the contacting step b).

In any of the preceding embodiments, the first probe can remain hybridized to the nucleic acid molecule prior to, during, and/or after the detection of the detectable signal from D2.

In any of the preceding embodiments, the method can avoid a step of removing the first probe or a portion thereof from the nucleic acid molecule by enzymatically cleaving, modifying, or degrading the first probe or portion thereof.

In any of the preceding embodiments, the method can avoid a step of inactivating the first probe or a portion thereof by removing or modifying the detectable moiety D1.

In any of the preceding embodiments, the method can avoid a step of cleaving a linker linking the detectable moiety D1 to the first probe.

In any of the preceding embodiments, the method can avoid a step of chemically or photochemically modifying the detectable moiety D1.

In any of the preceding embodiments, the method can avoid a step of bleaching the detectable moiety D1 by a chemical agent.

In any of the preceding embodiments, the method can avoid a step of photobleaching the detectable moiety D1.

In any of the preceding embodiments, the method can avoid a step of permanently and irreversibly extinguishing the detectable moiety D1.

In any of the preceding embodiments, the first probe and/or the second probe can be non-self-quenching. For example, the first probe and/or the second probe can be free of a secondary structure, such as a hairpin, that causes self-quenching of a detectable moiety by a quencher moiety in the same probe.

In any of the preceding embodiments, D1 and D2 can be the same or different detectable moieties, e.g., the same or different fluorophores. D1 and D2 can be fluorophores of the same or different emission wavelengths.

In any of the preceding embodiments, Q1 can be in proximity to D1 upon hybridization of H2 to H2', thereby quenching the detectable signal from D1.

In any of the preceding embodiments, Q1 may not be in sufficient proximity to D2 upon hybridization of H2 to H2' to quench the signal of D2 prior to detection.

In any of the preceding embodiments, the quencher and detectable moiety of a probe can be separated by at least 5 nucleotides up to about 50 nucleotides.

In any of the preceding embodiments, the detectable signal from D2 can be detected prior to, during, and/or after hybridization of H2 to H2'.

In any of the preceding embodiments, the detectable signal from D1 can be detected prior to hybridization of H2 to H2'.

In any of the preceding embodiments, upon hybridization of H2 to H2', the detectable signal from D1 may not detected while the detectable signal from D2 is detected.

In any of the preceding embodiments, the absorption spectrum of Q1 and the emission spectrum of D2 do not overlap.

In any of the preceding embodiments, D1 can be at the 3' end of the first probe, Q1 can be at the 5' end of the second probe, and D2 can be at the 3' end of the second probe.

In any of the preceding embodiments, D1 can be at the 5' end of the first probe, Q1 can be at the 3' end of the second probe, and D2 can be at the 5' end of the second probe.

In any of the preceding embodiments, the first probe and/or the second probe can be between about 10 and about 100 nucleotides in length, e.g., between about 15 and about 50 nucleotides in length.

In any of the preceding embodiments, D1 can remain in the biological sample, and the detectable signal from D1 is not detected in step b).

In any of the preceding embodiments, the detectable signal from D1 can be detected prior to step b).

In any of the preceding embodiments, the splint can comprise a region that hybridizes to the first probe.

In any of the preceding embodiments, the method can further comprise a step c) of contacting the biological sample with a third probe, wherein: the third probe comprises: (i) a hybridization sequence H3 that hybridizes to a hybridization sequence H3' of the nucleic acid molecule, the probe of the previous contacting step, or a splint, (ii) a quencher Q2, and (iii) a detectable moiety D3, and upon hybridization of H3 and H3', Q2 is in proximity to D2, thereby quenching the detectable signal from D2, wherein a detectable signal from D3 is detected in the biological sample.

In any of the preceding embodiments, the method can further comprise a step d) in a contacting step of a cycle number m (an integer of 4 or greater), contacting the biological sample with an additional probe Pm, wherein: the additional probe Pm comprises: (i) a hybridization sequence Hm that hybridizes to a hybridization sequence Hm' of the nucleic acid molecule, the probe of the previous contacting step, or a splint, (ii) a quencher Q(m−1), and (iii) a detectable moiety Dm, and upon hybridization of Hm and Hm', Q(m−1) is in proximity to a detectable moiety D(m−1) of the previous cycle, thereby quenching the detectable signal from D(m−1), wherein a detectable signal from Dm is detected in the biological sample.

In any of the preceding embodiments, D1 and D2 can remain in the biological sample and the detectable signals from D1 and D2 are not detected in step c) and/or step d).

In any of the preceding embodiments, the first probe, second probe, and/or Pm can be single-stranded linear oligonucleotide probes and may not form hairpin structures.

In any of the preceding embodiments, the quencher may not quench a detectable signal of the detectable moiety on the same probe.

In any of the preceding embodiments, the quenching in step b) and/or c) can be directed by hybridization of the probe.

In some aspects, provided herein is a method for analyzing a biological sample, comprising: a) contacting a biological sample with a probe in each of Cycles 1 to m, wherein: (1) Cycle 1 comprises contacting the biological sample with a first probe P1, wherein P1 comprises a detectable moiety D1 and a hybridization sequence H1, the biological sample comprises a nucleic acid molecule comprising a hybridization sequence H1', and H1' hybridizes to H1; (2) Cycle m comprises contacting the biological sample with a probe Pm, m is an integer, 2≤m, wherein Pm comprises a hybridization sequence Hm that hybridizes to a hybridization region Hm' of the nucleic acid molecule, a probe of a previous Cycle (m−1), or a splint, (ii) a quencher Q(m−1), and (iii) a detectable moiety Dm, and upon hybridization of Hm and Hm', Q(m−1) is in proximity to D(m−1), thereby quenching a detectable signal from a detectable moiety D(m−1) of the previous cycle, wherein a detectable signal from Dm is detected in the biological sample.

In any of the preceding embodiments, the method can comprise at least three cycles.

In any of the preceding embodiments, the splint can comprise a region that hybridizes to the probe P(m−1).

In some aspects, provided herein is a method for analyzing a biological sample, comprising: a) contacting a biological sample with a first probe, wherein: the first probe comprises a detectable moiety D1, and a hybridization sequence H1, the biological sample comprises a nucleic acid molecule comprising a hybridization sequence H1', a hybridization sequence H2', H1' hybridizes to H1; and b) contacting the biological sample with: (i) a second probe, wherein the second probe comprises a detectable moiety D2 and a hybridization sequence H2 that hybridizes to H2; and (ii) a first quencher probe Q1, wherein the first quencher probe comprises a region HQ1 that hybridizes to a quencher target region HQ1' of the first nucleic acid, the first probe, or a splint oligonucleotide that hybridizes to the first probe, and upon hybridization of HQ1 and HQ1', Q1 is in proximity to D1, thereby quenching a detectable signal from D1, wherein a detectable signal from D2 is detected in the biological sample.

In any of the preceding embodiments, the nucleic acid molecule can further comprise a hybridization sequence H3', and a hybridization sequence H4'.

In any of the preceding embodiments, the nucleic acid molecule can be a U-shaped probe, e.g., a probe that comprises a region that hybridizes to a target sequence flanked by overhangs on both the 5' and the 3' sides.

In any of the preceding embodiments, the method can further comprise contacting the biological sample with: (i) a third probe, wherein the third probe comprises a detectable moiety D3 and a hybridization sequence H3 that hybridizes to H3'; and (ii) a second quencher probe Q2, wherein the second quencher probe comprises a hybridization sequence HQ2 that hybridizes to HQ2; and upon hybridization of HQ2 and HQ2', Q2 is in proximity to D2, thereby quenching a detectable signal from D2, wherein a detectable signal from D3 is detected in the biological sample.

In any of the preceding embodiments, the method can further comprise contacting the biological sample with: (i) a fourth probe, wherein the fourth probe comprises a detectable moiety D4 and a hybridization sequence H4 that hybridizes to H4'; and (ii) a second quencher probe Q3, wherein the second quencher probe comprises a hybridization sequence HQ3 that hybridizes to HQ3; and upon hybridization of HQ3 and HQ3', Q3 is in proximity to D3, thereby quenching a detectable signal from D3, wherein a detectable signal from D4 is detected in the biological sample.

In any of the preceding embodiments, the first detectable moiety D1 can be detected in the first contacting step and not detected in the second contacting step. In some embodiments, the second detectable moiety D2 can be detected in the second contacting step and not detected in the first contacting step. In some embodiments an additional detectable moiety can be detected in a subsequent contacting step, whereby a sequential signature of detectable signals is generated.

In any of the preceding embodiments, the nucleic acid molecule can be endogenous in the biological sample.

In any of the preceding embodiments, the nucleic acid molecule can be exogenous to the biological sample.

In any of the preceding embodiments, the nucleic acid molecule in the biological sample can comprise one or more barcode sequences.

In any of the preceding embodiments, the nucleic acid molecule in the biological sample can be DNA or RNA.

In any of the preceding embodiments, the nucleic acid molecule in the biological sample can be a probe that hybridizes to an mRNA molecule, a cDNA molecule, a labelling agent that directly or indirectly binds to an analyte in the biological sample, and/or a product (e.g., a hybridization product, a ligation product, an extension product (e.g., by a DNA or RNA polymerase), a replication product, a transcription/reverse transcription product, and/or an amplification product such as a rolling circle amplification (RCA) product) of the mRNA molecule, the cDNA molecule, or the labelling agent. In some instances, the nucleic acid molecule in the biological sample is a probe that hybridizes to an analyte (e.g., mRNA) in the biological sample.

In any of the preceding embodiments, the labelling agent can comprise a reporter oligonucleotide comprising one or more barcode sequences, and the amplification product can comprise multiple copies of the one or more barcode sequences.

In any of the preceding embodiments, the nucleic acid molecule in the biological sample can be a probe that hybridizes to a rolling circle amplification (RCA) product of a circular or circularizable (e.g., padlock) probe that hybridizes to a DNA (e.g., genomic DNA or a cDNA of an mRNA) or RNA analyte (e.g., an mRNA) in the biological sample.

In any of the preceding embodiments, the labelling agent can bind to a non-nucleic acid analyte in the sample, e.g., a protein analyte, a carbohydrate analyte, and/or a lipid analyte. In some embodiments, the labelling agent can comprise an antibody or antigen binding fragment thereof that binds to a protein analyte, and the nucleic acid molecule in the biological sample can be a rolling circle amplification (RCA) product of a circular or padlock probe that hybridizes to a reporter oligonucleotide of the labelling agent.

In any of the preceding embodiments, the biological sample can be a processed or cleared biological sample.

In any of the preceding embodiments, the biological sample can be a tissue sample. In some embodiments, the tissue sample can be a tissue slice between about 1 µm and about 50 µm in thickness. In some embodiments, the tissue slice is between about 5 µm and about 35 µm in thickness. In some embodiments, the tissue sample is embedded in a matrix. In some embodiments, the matrix comprises a hydrogel. In any of the preceding embodiments, the biological sample can be fixed or not fixed. In any of the preceding embodiments, the biological sample can be a formalin-fixed, paraffin-embedded (FFPE) sample, a frozen tissue sample, or a fresh tissue sample. In any of the preceding embodiments, the biological sample can be permeabilized.

In some aspects, provided herein is a hybridization complex comprising: (i) a nucleic acid molecule comprising a hybridization sequence H1', and H1' hybridizes to H1; (ii) a first probe comprising a detectable moiety D1 and a hybridization sequence H1, and (iii) a second probe comprising a hybridization sequence H2 that is hybridized to a hybridization region H2' of the nucleic acid molecule and/or hybridized to the first probe, a quencher Q1, and a detectable moiety D2, wherein the quencher Q1 is in proximity with the detectable moiety D1 of the hybridization complex, wherein a detectable signal from D2 can be detected from the hybridization complex.

In any of the preceding embodiments, the second probe can be a single molecule.

In any of the preceding embodiments, the second probe can comprise a quencher probe comprising the quencher Q1 and a detection probe comprising the detectable moiety D2, wherein the quencher probe and the detection probe are separate molecules.

In any of the preceding embodiments, the second probe can further comprise a splint oligonucleotide that hybridizes to the quencher probe and the detection probe.

In any of the preceding embodiments, the quencher and detectable moiety of the second probe can be separated by at least 5 nucleotides up to about 50 nucleotides.

In any of the preceding embodiments, the complex can further comprise a third probe, wherein the third probe comprises: (i) a hybridization sequence H3 that is hybridized to a hybridization region H3' of the nucleic acid molecule or the second probe, (ii) a quencher Q2, and (iii) a detectable moiety D3, wherein the quencher Q2 is in proximity to D2 in the hybridization complex, wherein a detectable signal from D3 can be detected from the hybridization complex.

In some aspects, disclosed herein is a kit for analyzing a biological sample, comprising: a) a first probe P1, wherein the first probe comprises a detectable moiety D1 and a hybridization sequence H1, wherein H1 is capable of hybridizing to a sequence H1' in a target nucleic acid; and b) a second probe P2, wherein the second probe comprises a detectable moiety D2, a hybridization sequence H2, wherein H2 is capable of hybridizing to a sequence H2' in the target nucleic acid or the first probe P1, and a hybridization sequence H3' for hybridizing to a subsequent probe. In some embodiments, the second probe comprises a quencher Q1 that does not quench detectable moiety D2 but quenches detectable moiety D1 upon hybridization of H2 and H2'. In some embodiments, the kit further comprises c) one more subsequent probes Pn designed to contact the biological sample in subsequent contacting steps of a method disclosed herein, wherein n is an integer of 3 or greater, wherein the one or more subsequent probes Pn each comprises (i) a detectable moiety Dn, (ii) a hybridization sequence Hn, wherein Hn is capable of hybridizing to a hybridization sequence Hn' in a probe P(n−1) of the previous cycle, and (iii) a quencher Q(n−1) that does not quench detectable moiety Dn, and upon hybridization of Hn and Hn', quencher Q(n−1) is in proximity to detectable moiety D(n−1) of probe P(n−1), and is thus capable of quenching the detectable signal from D(n−1). In any of the preceding embodiments, the first, second, and one more subsequent probes can be non-self-quenching.

Figure 1:
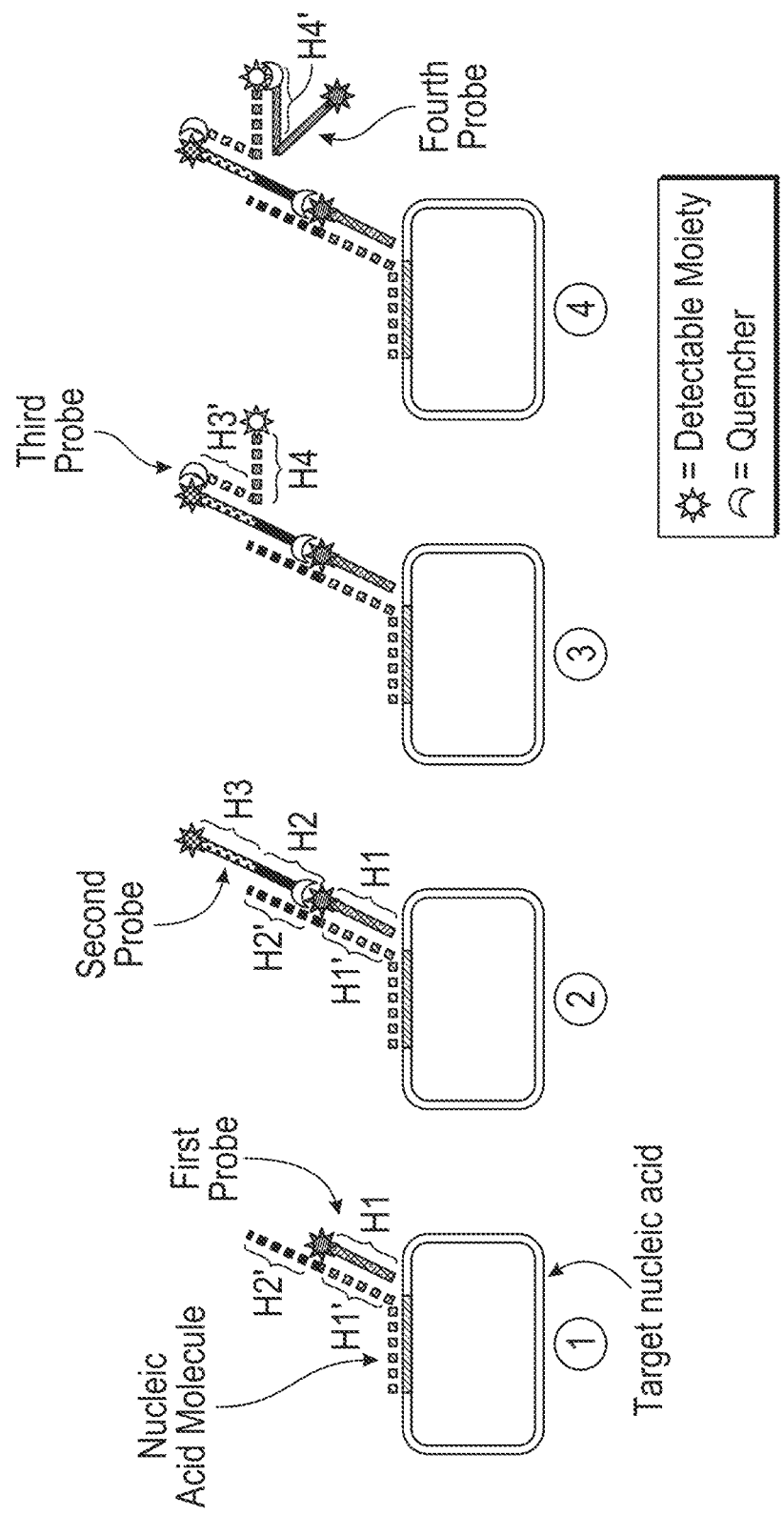
FIG. 1 shows exemplary hybridization complexes formed in a first (1), second (2), third (3), and fourth (4) contacting steps. The nucleic acid molecule (e.g., a probe such as an L-shaped or U-shaped probe) comprises a landing sequence for hybridizing to both the first and the second probes (H1' and H2', respectively), and the second probe comprises a landing sequence (H3) for hybridizing to the third probe, which in turn comprises a landing sequence (H4) for hybridizing to the fourth probe. The detectable moiety of a probe is quenched by a quencher of the next probe, eliminating the signal without physically removing the probe (e.g., by stripping under denaturing conditions such as by using formamide and/or heating), cleaving the detectable moiety of the probe, and/or photobleaching. The nucleic acid molecule can be a probe hybridized to a target nucleic acid in the sample. The target nucleic acid can be any target nucleic acid described herein (e.g., an endogenous analyte, a labelling agent, or a product of an endogenous analyte or labelling agent, such as a hybridization, ligation, or extension product). In some examples, the target nucleic acid is a rolling circle amplification product. In other examples, the target nucleic acid is a nucleic acid analyte such as an mRNA. The nucleic acid molecule (e.g., a probe, which can be a primary probe) can be hybridized to a barcode sequence or marker sequence in the target nucleic acid.

In any of FIGS. 1-6, the nucleic acid molecule may be a probe that binds to another probe (e.g., circular probe shown as an example) or may be a probe that binds to a product of an analyte (e.g., mRNA or cDNA) or a product of another probe that binds to the analyte, such as an RCA product.

DETAILED DESCRIPTION

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Existing methods of decoding a sequence in a target nucleic acid by sequential hybridization of detectably labeled probes require removal of the hybridized labeled detection probe or detectable moiety once it has been imaged. The process of removing the hybridized probe or detectable moiety can be difficult. This step often involves the use of high temperature and/or potentially toxic chemical agents such as formamide in the case of probe removal (stripping). Alternative methods of removing a detectable signal such as photobleaching, chemical deactivation, and chemical cleavage of the fluorophores (e.g., disulfide cleavage), enzymatic cleavage (using, for example, an exonuclease, endonuclease, protease, or USER™ (Uracil-Specific Excision Reagent) cleavage system) typically require a separate removal step. While these methods may avoid some of the damage to the biological sample caused by probe stripping, they also add to the time required to perform the method.

In view of these issues, there is a desire for alternative methods of performing an assay for detecting analytes (e.g., including coding and decoding nucleotide barcode sequences), particularly cost- and time-efficient methods which are suitable for high multiplicity scenarios, and which provide high specificity and accuracy without damaging the sample of target nucleic acid molecules which are being analyzed. The present application provides a method of decoding comprising sequence hybridization-directed quenching of the detectable moieties of earlier hybridized probes, thus providing an alternative decoding approach that reduces or eliminates the need for damaging probe stripping. Furthermore, in some embodiments, the methods and compositions provided herein obviate the need for a separate step to remove the detectable signal or moiety of a probe once it has been imaged. As such, the methods and compositions provided herein can provide a more efficient method of detecting a sequence in a target nucleic acid.

In some embodiments, a method disclosed herein comprises profiling analytes (or products or derivatives thereof) including their spatial information (e.g., localization of the analyte), such as the transcriptome or a subset thereof, in a biological sample. Methods, compositions, kits, devices, and systems for these in situ assays, including in situ genomics and transcriptomics assays, are provided. Also provided herein are compositions and methods for detecting and/or quantifying nucleic acids in cells, tissues, organs or organisms. In some embodiments, the present disclosure provides methods of analyzing the position and/or identity of an analyte by sequential hybridization of detectably labeled probes, wherein the cycles of sequential hybridization do not require a separate removal step to remove the detectable signal or moiety of a probe once it has been imaged.

In some embodiments, disclosed herein is a method for analyzing a biological sample, comprising: a) contacting a biological sample with a first probe, wherein: the first probe comprises a detectable moiety D1 and a hybridization sequence H1, the biological sample comprises a nucleic acid molecule comprising a hybridization sequence H1', and H1' hybridizes to H1; and b) contacting the biological sample with a second probe, wherein: the second probe comprises: (i) a hybridization sequence H2 that hybridizes to a hybridization region H2' of the nucleic acid molecule, the first probe, or a splint, (ii) a quencher Q1, and (iii) a detectable moiety D2, and upon hybridization of H2 and H2', Q1 is in proximity to D1, thereby quenching a detectable signal from D1, wherein a detectable signal from D2 is detected in the biological sample.

In some embodiments, provided herein is a method for analyzing a biological sample, comprising: a) contacting a biological sample with a first probe, wherein: the first probe comprises a detectable moiety D1 and a hybridization sequence H1, the biological sample comprises a nucleic acid molecule comprising a hybridization sequence H1', and H1' hybridizes to H1, wherein a detectable signal from D1 is detected in the biological sample; b) contacting the biological sample with a second probe, wherein: the second probe comprises: (i) a hybridization sequence H2 that hybridizes to a hybridization region H2' of the nucleic acid molecule, the first probe, or a splint, (ii) a quencher Q1, and (iii) a detectable moiety D2, and upon hybridization of H2 and H2', Q1 is in proximity to D1, thereby quenching a detectable signal from D1, wherein a detectable signal from D2 is detected in the biological sample; and c) contacting the biological sample with a third probe, wherein: the third probe comprises: (i) a hybridization sequence H3 that hybridizes to a hybridization sequence H3' of the nucleic acid molecule, the probe of the previous contacting step, or a splint, (ii) a quencher Q2, and (iii) a detectable moiety D3, and upon hybridization of H3 and H3', Q2 is in proximity to D2, thereby quenching the detectable signal from D2, wherein a detectable signal from D3 is detected in the biological sample.

In some embodiments, disclosed herein is a method for analyzing a biological sample, comprising: a) contacting a biological sample with a probe in each of Cycles 1 to m, wherein: Cycle 1 comprises contacting the biological sample with a first probe P1, wherein P1 comprises a detectable moiety D1 and a hybridization sequence H1, the biological sample comprises a nucleic acid molecule comprising a hybridization sequence H1', and H1' hybridizes to H1; Cycle m comprises contacting the biological sample with a probe Pm, m is an integer, 2≤m, wherein Pm comprises a hybridization sequence Hm that hybridizes to a hybridization region Hm' of the nucleic acid molecule, a probe of a previous Cycle (m−1), or a splint, (ii) a quencher Q(m−1), and (iii) a detectable moiety Dm, and upon hybridization of Hm and Hm', Q(m−1) is in proximity to D(m−1), thereby quenching a detectable signal from a detectable moiety D(m−1) of the previous cycle, wherein a detectable signal from Dm is detected in the biological sample.

In some embodiments, a method provided herein comprises: a) contacting a biological sample with a first probe, wherein: the first probe comprises a detectable moiety D1, and a hybridization sequence H1, the biological sample comprises a nucleic acid molecule comprising a hybridization sequence H1', a hybridization sequence H2', H1' hybridizes to H1; and b) contacting the biological sample with: (i) a second probe, wherein the second probe comprises a detectable moiety D2 and a hybridization sequence H2 that hybridizes to H2'; and (ii) a first quencher probe Q1, wherein the first quencher probe comprises a region HQ1 that hybridizes to a quencher target region HQ1' of the first nucleic acid, the first probe, or a splint oligonucleotide that hybridizes to the first probe, and upon hybridization of HQ1 and HQ1', Q1 is in proximity to D1, thereby quenching a detectable signal from D1, wherein a detectable signal from D2 is detected in the biological sample.

In some embodiments, the method addresses one or more issues relating to sequential hybridization of detectably labeled probes. For example, in some embodiments, a separate removal step to remove or inactivate a detectable moiety is not required by the methods provided herein. In some instances, any number of detectable moieties that have already been imaged remain in the sample (e.g., within a hybridization complex), but are not detected in subsequent imaging steps. The use of a quencher conjugated to a probe (e.g., oligonucleotide) that is guided by sequence-specific hybridization can enable specific quenching of the desired detectable moiety (e.g., an already-imaged detectable moiety), even when the quencher is added in the same contacting step as a detectably labeled probe to be imaged. In some embodiments, the quencher and the detectable moiety can be conjugated to the same probe. In some embodiments, the quencher and the detectable moiety of a given probe are separated by a distance that is sufficient to prevent quenching of the detectable moiety on the same probe (e.g., to prevent quenching of D2 by Q1 after hybridization). In some embodiments, the probe comprising a quencher and a detectable moiety does not form a secondary structure (e.g., a hairpin or stem-loop structure), and does not quench the detectable moiety before hybridization.

In some embodiments, a composition disclosed herein provides a hybridization complex prepared according to any one of the methods provided herein. In some embodiments, a hybridization complex provided herein comprises: (i) a nucleic acid molecule comprising a hybridization sequence H1', and H1' hybridizes to H1; (ii) a first probe comprising a detectable moiety D1 and a hybridization sequence H1, and (iii) a second probe comprising a hybridization sequence H2 that is hybridized to a hybridization region H2' of the nucleic acid molecule and/or hybridized to the first probe, a quencher Q1, and a detectable moiety D2, wherein the quencher Q1 is in proximity with the detectable moiety D1 of the hybridization complex, wherein a detectable signal from D2 can be detected from the hybridization complex. In some embodiments, the complex further comprises a third probe, wherein the third probe comprises: a hybridization sequence H3 that is hybridized to a hybridization region H3' of the nucleic acid molecule or the second probe, a quencher Q2, and a detectable moiety D3, wherein the quencher Q2 is in proximity to D2 in the hybridization complex, wherein a detectable signal from D3 can be detected from the hybridization complex.

Kits for performing any of the methods disclosed herein are also provided. In some embodiments, provided herein is a kit for analyzing a biological sample, the kit comprising a first probe P1, wherein the first probe comprises a detectable moiety D1 and a hybridization sequence H1, wherein H1 is capable of hybridizing to a sequence H1' in a target nucleic acid. In some embodiments, the kit further comprises a second probe P2, wherein the second probe comprises a detectable moiety D2, a hybridization sequence H2, wherein H2 is capable of hybridizing to a sequence H2' in the target nucleic acid or the first probe P1, and a hybridization sequence H3' for hybridizing to a subsequent probe. In some embodiments, the second probe P2 further comprises a quencher Q1 that does not quench detectable moiety D2 but quenches detectable moiety D1 upon hybridization of H2 and H2'. In some embodiments, the kit further comprises one more subsequent probes Pn designed to contact the biological sample in subsequent contacting steps of a method disclosed herein, wherein n is an integer of 3 or greater, wherein the one or more subsequent probes Pn each comprises (i) a detectable moiety Dn, (ii) a hybridization sequence Hn, wherein Hn is capable of hybridizing to a hybridization sequence Hn' in a probe P(n−1) of the previous cycle, and (iii) a quencher Q(n−1) that does not quench detectable moiety Dn, and upon hybridization of Hn and Hn', quencher Q(n−1) is in proximity to detectable moiety D(n−1) of probe P(n−1), and is thus capable of quenching the detectable signal from D(n−1). In some embodiments, a kit comprises a plurality of probes for use in cycles of detection and for targeting a plurality of target analytes in a sample.

Nucleic acids and/or analytes that can be analyzed by the presently disclosed methods are described in greater detail in Section II.

II. Samples, Analytes, and Target Sequences

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed, e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 µm to about 2 mm.

Additional methods and aspects of hydrogel embedding of biological samples are described for example in Chen et al., *Science* 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, crosslinking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, Mass.), Label-IT Amine (available from MirusBio, Madison, Wis.) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation method known in the art. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete.

In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents.

Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some embodiments, one or more nucleic acid probes can be used to hybridize to a target nucleic acid (e.g., cDNA or RNA molecule, such as an mRNA) and ligated in a templated ligation reaction (e.g., RNA-templated ligation (RTL) or DNA-templated ligation (e.g., on cDNA)) to generate a product for analysis. In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques,* 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific subcellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer binding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed.

(a) Hybridization

In some embodiments, a product of an endogenous analyte and/or a labelling agent is a hybridization product comprising the pairing of substantially complementary or complementary nucleic acid sequences within two different molecules, one of which is the endogenous analyte or the labelling agent (e.g., reporter oligonucleotide attached thereto). The other molecule can be another endogenous molecule or another labelling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various probes and probe sets can be hybridized to an endogenous analyte and/or a labelling agent and each probe may comprise one or more barcode sequences. Exemplary barcoded probes include L-shaped probes (probes comprising a region that hybridizes to an analyte in the sample and an overhang region, which may comprise one or more barcode sequences) and U-shaped probes (probes comprising a region that hybridizes to an analyte in the sample and two overhang regions, which may comprise one or more barcode sequences). Exemplary barcoded probes or probe sets may also be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary.

(b) Ligation

In some embodiments, a product of an endogenous analyte and/or a labelling agent is a ligation product. In some embodiments, the ligation product is formed between two or more endogenous analytes. In some embodiments, the ligation product is formed between an endogenous analyte and a labelling agent. In some embodiments, the ligation product is formed between two or more labelling agent. In some embodiments, the ligation product is an intramolecular ligation of an endogenous analyte. In some embodiments, the ligation product is an intramolecular ligation of a labelling agent, for example, the circularization of a circularizable probe or probe set upon hybridization to a target sequence. The target sequence can be comprised in an endogenous analyte (e.g., nucleic acid such as a genomic DNA or mRNA) or a product thereof (e.g., cDNA from a cellular mRNA transcript), or in a labelling agent (e.g., the reporter oligonucleotide) or a product thereof.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety. In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety. In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature (Tm) of the DNA strands. This selectively reduces the concentration of annealed mismatched substrates (expected to have a slightly lower Tm around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(c) Primer Extension and Amplification

In some embodiments, a product is a primer extension product of an analyte, a labelling agent, a probe or probe set bound to the analyte (e.g., a padlock probe bound to genomic DNA, mRNA, or cDNA), or a probe or probe set bound to the labelling agent (e.g., a padlock probe bound to one or more reporter oligonucleotides from the same or different labelling agents).

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. A primer extension reaction generally refers to any method where two nucleic acid sequences become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-119, 2000; Faruqi et al, BMC Genomics 2:4, 2000; Nallur et al, Nucl. Acids Res. 29:el 18, 2001; Dean et al. Genome Res. 11:1095-1099, 2001; Schweitzer et al, Nature Biotech. 20:359-365, 2002; U.S. Pat. Nos. 6,054, 274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, US 2018/0051322, WO 2017/079406, US 2018/251833, US 2016/0024555, US 2018/0251833 and US 2017/0219465, the contents of each of which are herein incorporated by reference in their entirety. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. As noted above, many assays are known for the detection of numerous different analytes, which use a RCA-based detection system, e.g., where the signal is provided by generating a RCP from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (i.e. a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some embodiments, a product herein includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a probe disclosed herein (e.g., a detectably labelled probe comprising a quencher moiety) may be a hybridization complex formed of a cellular nucleic acid in a sample and an exogenously added nucleic acid probe. The exogenously added nucleic acid probe may comprise an overhang that does not hybridize to the cellular nucleic acid but hybridizes to another probe (e.g., a detectably labelled comprising a quencher moiety). The exogenously added nucleic acid probe may be optionally ligated to a cellular nucleic acid molecule or another exogenous nucleic acid molecule. In other examples, a product comprising a target sequence for a probe disclosed herein (e.g., a detectably labelled probe comprising a quencher moiety) may be an RCP of a circularizable probe or probe set which hybridizes to a cellular nucleic acid molecule (e.g., genomic DNA or mRNA) or product thereof (e.g., a transcript such as cDNA, a DNA-templated ligation product of two probes, or an RNA-templated ligation product of two probes). In other examples, a product comprising a target sequence for a probe disclosed herein (e.g., a detectably labelled probe comprising a quencher moiety) may a probe hybridizing to an RCP. The probe may comprise an overhang that does not hybridize to the RCP but hybridizes to another probe (e.g., a detectably labelled probe comprising a quencher moiety). The probe may be optionally ligated to a cellular nucleic acid molecule or another probe, e.g., an anchor probe that hybridize to the RCP.

C. Target Sequences

A target sequence for a probe disclosed herein (e.g., a detectably labelled probe comprising a quencher moiety) may be comprised in any analyte disclose herein, including an endogenous analyte (e.g., a viral or cellular nucleic acid), a labelling agent, or a product (e.g., a hybridization, ligation, or extension product) of an endogenous analyte and/or a labelling agent.

In some embodiments, a target sequence for a detectably labelled probe comprising a quencher moiety is in a primary probe hybridized to an analyte in the sample. In some embodiments, the primary probe is hybridized to a marker sequence for a given analyte. A marker sequence is a sequence that identifies a given analyte (e.g., alone or in combination with other marker sequences). The marker sequence (or combination of marker sequences) for a given target analyte can therefore be specific to that analyte, or unique, such that multiple target analytes can be distinguished from each other. A "marker sequence" is thus a sequence which marks, is associated with, or identifies a given analyte. It is a sequence by which a given analyte may be detected and distinguished from other analytes. Where an "analyte" comprises a group of related molecules e.g. isoforms or variants or mutants etc., or molecules in a particular class or group, it is not required that a marker is unique or specific to only one particular analyte molecule, and it may be used to denote or identify the analyte as a group. However, where desired, a marker sequence may be unique or specific to a particular specific analyte molecule, e.g. a particular variant. In this way different variants, or isoforms, or mutants may be identified or distinguished from one another.

In some embodiments, a group of primary nucleic acid probes hybridize to a group of marker sequences in a target nucleic acid molecule, such as an RNA (e.g., mRNA). For example, a group of primary nucleic acid probes described herein can be designed to hybridize to a plurality of marker sequences present in the nucleic acid molecule. In some embodiments, the target nucleic acid comprises between or between about 10 and 20, 10 and 15, 10 and 30, 20 and 30, 20 and 40, 20 and 50, 40 and 50, or 45 and 60 marker sequences. The marker sequences can comprise copies of the same sequence and/or can comprise different sequences. Hybridization of a plurality of primary nucleic acid probes to a given target nucleic acid increases the number of binding sites available for hybridization of labelled probes according to the methods described herein (e.g., hybridization of a detectably labelled probe comprising a quencher moiety). In some embodiments, a plurality of primary nucleic acid probes that hybridizes to each given target nucleic acid share the same barcode sequences. In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding embodiments, barcodes (e.g., primary and/or secondary barcode sequences) can be analyzed (e.g., detected or sequenced) using any suitable methods or techniques, including those described herein or by modifying other detection methods, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, hybridization-based in situ sequencing (HybISS). In some embodiments, the methods may be combined with other techniques such as targeted in situ sequencing, fluorescent in situ sequencing (FISSEQ), sequencing by synthesis (SBS), sequencing by ligation (SBL), sequencing by hybridization (SBH). In some embodiments, barcodes (e.g., primary and/or secondary barcode sequences) can be analyzed (e.g., detected or sequenced) by modifying other detection methods, such as those described in spatially-resolved transcript amplicon readout mapping (STARmap). In any of the preceding embodiments, the methods provided herein can include analyzing the barcodes by sequential hybridization and detection with a plurality of labelled probes (e.g., detection oligos). For example, sequential hybridization and detection may comprise detection (directly or indirectly) and quenching of signals associated with the analyte.

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and US 2021/0164039, which are hereby incorporated by reference in their entirety.

III. Probes

Standard in situ transcriptomic techniques (e.g., HybISS and SeqFISH+) employ strategies for optically encoding the spatial location of target analytes (e.g., mRNAs) in a sample using sequential rounds of fluorescent hybridization, as described herein. Microcopy is used to detect a signals (e.g., 4 or 5 fluorescent colors) indicative of the spatial localization of a target, including various rounds of hybridization and stripping, in order to generate a large set of unique optical signal signatures assigned to different analytes. These methods often require a large number of hybridization rounds, and a large number of microscope lasers (e.g., detection channels) to detect a large number of fluorophores, resulting in a one to one mapping of the lasers to the fluorophores. Specifically, each detectably-labeled probe comprises one detectable moiety, e.g., a fluorophore.

In some embodiments, provided herein are assays for profiling analytes (or products or derivatives thereof) including their spatial information (e.g., localization of the analyte) in a biological sample using probes, wherein the assay involves detection (directly or indirectly) and quenching of signals associated with the analyte. Methods, compositions, kits, devices, and systems for these in situ assays, including in situ genomics and transcriptomics assays, are provided. In some embodiments, the present disclosure provides methods of analyzing the position and/or identity of an analyte by sequential hybridization of detectably labeled probes, wherein the cycles of sequential hybridization do not require a separate removal step to remove the detectable signal or moiety of a probe once it has been imaged.

In some embodiments, the probes or probe complexes provided herein comprise a detectable component (e.g., a detectable moiety) and a quencher component (e.g., a quenching moiety). The detectable component may provide a signal to be detected that is associated with the analyte while the quencher component may allow a previous (e.g., an already detected) signal to be removed, thereby allowing a signal of a subsequent cycle to be detected effectively. In some embodiments, the quenching of a previous signal occurs in the same step as the detection of the subsequent signal. In some cases, a probe can have both a detectable component and a quencher component on a molecule (e.g., a single oligonucleotide). In some cases, a set of probes (e.g., that can form a complex) may have a detectable component on one molecule (e.g., oligonucleotide) and a quencher component on another molecule (e.g., oligonucleotide), wherein the two molecules may be associated in a complex upon hybridization (e.g., which can be further mediated by a splint molecule). In some aspects, both the quencher and detectable components are associated with an oligonucleotide such that the hybridization of such molecules with their targets are directed and/or sequence specific.

In some aspects, various design of the hybridization regions may be used to allow a branched hybridization complex to form comprising the nucleic acid molecule and two or more probes. In some embodiments, disclosed herein is a method for analyzing a biological sample, comprising contacting a biological sample with a probe comprising a detectable moiety D1 and a hybridization sequence H1 for hybridizing to a nucleic acid molecule comprising a hybridization sequence H1', and H1' hybridizes to H1, the method also includes contacting the biological sample with a second probe, wherein the second probe comprises a hybridization sequence H2. In some cases, H2 of the second probe may hybridize to a hybridization region H2' of the nucleic acid molecule, a sequence of the first probe, or a sequence of a splint molecule. The second probe may also comprise a quencher Q1 and a detectable moiety D2. In some embodiments, upon hybridization of H2 and H2', Q1 is in proximity to D1 and quenches a detectable signal from D1, and a detectable signal from D2 can be further detected in the biological sample.

In some examples, the target nucleic acid for the probes described herein is an L-shaped or U-shaped probe that binds to an analyte. In some examples, the target nucleic acid for the probes described herein is a barcode sequence in a probe that binds to an analyte, or in a product thereof (e.g., a barcode sequence in an RCP generated using a primary probe that hybridizes to an endogenous nucleic acid in a sample as template). In some embodiments, the L-shaped or U-shaped probe comprises a region that hybridizes to a barcode sequence in a labelling agent or another probe or product thereof or to an analyte (e.g., a nucleic acid analyte in the sample). In some embodiments, the nucleic acid molecule sequence hybridized by the probes disclosed herein which comprise a detectable moiety and a quencher moiety may be a sequence of a primary probe or a sequence of a product of the primary probe (e.g., a hybridization product, a ligation product, an extension product, an amplification product). In some instances, the probes comprising a detectable moiety and a quencher moiety binds directly to a primary probe or indirectly to a primary probe via an intermediate probe.

The nucleic acid probes and/or probe sets disclosed herein can be introduced into a cell or used to otherwise contact a biological sample such as a tissue sample. The probes (e.g., the primary probes disclosed herein and/or any detectable probe disclosed herein, e.g., for FISH and/or RCA-based detection) may comprise any of a variety of entities that can hybridize to a nucleic acid, typically by Watson-Crick base pairing, such as DNA, RNA, LNA, PNA, etc. The nucleic acid probe may comprise a targeting sequence that is able to directly or indirectly bind to at least a portion of a target nucleic acid. The nucleic acid probe may be able to bind to a specific target nucleic acid (e.g., an mRNA, or other nucleic acids disclosed herein). In some embodiments, the nucleic acid probes may be detected using a detectable label, and/or by using secondary nucleic acid probes able to bind to the nucleic acid probes. In some embodiments, the nucleic acid probes (e.g., primary probes and/or secondary probes) are compatible with one or more biological and/or chemical reactions. For instance, a nucleic acid probe disclosed herein can serve as a template or primer for a polymerase, a template or substrate for a ligase, a substrate for a click chemistry reaction, and/or a substrate for a nuclease (e.g., endonuclease or exonuclease for cleavage or digestion).

In some embodiments, more than one type of primary nucleic acid probes may be contacted with a sample, e.g., simultaneously or sequentially in any suitable order, such as in sequential probe hybridization/unhybridization cycles. In some embodiments, more than one type of secondary nucleic acid probes may be contacted with a sample, e.g., simultaneously or sequentially in any suitable order, such as in sequential probe hybridization/unhybridization cycles. In some embodiments, the secondary probes may comprise probes that bind to a product of a primary probe targeting an analyte. In some embodiments, more than one type of higher order nucleic acid probes may be contacted with a sample, e.g., simultaneously or sequentially in any suitable order, such as in sequential probe hybridization/unhybridization cycles. In some embodiments, more than one type of detectably labeled nucleic acid probes (e.g., one or more primary detectable probes for smFISH readout and/or one or more secondary detectable probes for RCA readout) may be contacted with a sample, e.g., simultaneously or sequentially in any suitable order, such as in sequential probe hybridization/unhybridization cycles. In some embodiments, the detectably labeled nucleic acid probes can be used for smFISH readout and/or for RCA readout. In some embodiments, the detectably labeled probes (e.g., one or more primary detectable probes for smFISH readout and/or one or more secondary detectable probes for RCA readout) may comprise probes that bind to one or more primary probes, one or more secondary probes, one or more higher order probes, one or more intermediate probes between a primary/secondary/higher order probes, and/or one or more detectably or non-detectably labeled probes (e.g., as in the case of a hybridization chain reaction (HCR), a branched DNA reaction (bDNA), or the like). In some embodiments, at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid probes (e.g., primary, secondary, higher order probes, and/or detectably labeled probes) can be contacted with a sample, e.g., simultaneously or sequentially in any suitable order. Between any of the probe contacting steps disclosed herein, the method may comprise one or more intervening reactions and/or processing steps, such as modifications of a target nucleic acid, modifications of a probe or product thereof (e.g., via hybridization, ligation, extension, amplification, cleavage, digestion, branch migration, primer exchange reaction, click chemistry reaction, crosslinking, attachment of a detectable label, activating photo-reactive moieties, etc.), removal of a probe or product thereof (e.g., cleaving off a portion of a probe and/or unhybridizing the entire probe), signal modifications (e.g., quenching, masking, photobleaching, signal enhancement (e.g., via FRET), signal amplification, etc.), signal removal (e.g., cleaving off or permanently inactivating a detectable label), crosslinking, de-crosslinking, and/or signal detection.

The target-binding sequence (sometimes also referred to as the targeting region/sequence, the recognition region/sequence, or the hybridization region/sequence) of a probe may be positioned anywhere within the probe. For instance, the target-binding sequence of a primary probe that binds to a target nucleic acid can be 5' or 3' to any barcode sequence in the primary probe. Likewise, the target-binding sequence of a secondary probe (which binds to a primary probe or complement or product thereof) can be 5' or 3' to any barcode sequence in the secondary probe. In some embodiments, the target-binding sequence may comprise a sequence that is substantially complementary to a portion of a target nucleic acid. In some embodiments, the portions may be at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary.

The target-binding sequence of a primary nucleic acid probe may be determined with reference to a target nucleic acid (e.g., a cellular RNA or a reporter oligonucleotide of a labelling agent for a cellular analyte) that is present or suspected of being present in a sample. In some embodiments, more than one target-binding sequence can be used to identify a particular analyte comprising or associated with a target nucleic acid. The more than one target-binding sequence can be in the same probe or in different probes. For instance, multiple probes can be used, sequentially and/or simultaneously, that can bind to (e.g., hybridize to) different regions of the same target nucleic acid. In other examples, a probe may comprise target-binding sequences that can bind to different target nucleic acid sequences, e.g., various intron and/or exon sequences of the same gene (for detecting splice variants, for example), or sequences of different genes, e.g., for detecting a product that comprises the different target nucleic acid sequences, such as a genome rearrangement (e.g., inversion, transposition, translocation, insertion, deletion, duplication, and/or amplification).

After contacting the nucleic acid probes with a sample, the probes may be directly detected by determining detectable labels (if present), and/or detected by using one or more other probes that bind directly or indirectly to the probes or products thereof. The one or more other probes may comprise a detectable label. For instance, a primary nucleic acid probe can bind to a target nucleic acid in the sample, and a secondary nucleic acid probe can be introduced to bind to the primary nucleic acid probe, where the secondary nucleic acid probe or a product thereof can then be detected using detectable probes (e.g., detectably labeled probes). Higher order probes that directly or indirectly bind to the secondary nucleic acid probe or product thereof may also be used, and the higher order probes or products thereof can then be detected using detectably labeled probes.

In some instances, a secondary nucleic acid probe binds to a primary nucleic acid probe directly hybridized to the target nucleic acid. A secondary nucleic acid probe (e.g., a primary detectable probe or a secondary detectable probe disclosed herein) may contain a recognition sequence able to bind to or hybridize with a primary nucleic acid probe or a product thereof (e.g., an RCA product), e.g., at a barcode sequence or portion(s) thereof of the primary nucleic acid probe or product thereof. In some embodiments, a secondary nucleic acid probe may bind to a combination of barcode sequences (which may be continuous or spaced from one another) in a primary nucleic acid probe, a product thereof, or a combination of primary nucleic acid probes. In some embodiments, the binding is specific, or the binding may be such that a recognition sequence preferentially binds to or hybridizes with only one of the barcode sequences or complements thereof that are present. The secondary nucleic acid probe may also contain one or more detectable labels. If more than one secondary nucleic acid probe is used, the detectable labels may be the same or different.

The recognition sequences may be of any length, and multiple recognition sequences in the same or different secondary nucleic acid probes may be of the same or different lengths. If more than one recognition sequence is used, the recognition sequences may independently have the same or different lengths. For instance, the recognition sequence may be at least 4, at least 5, least 6, least 7, least 8, least 9, at least 10, at least 11, at least 12, least 13, least 14, at least 15, least 16, least 17, least 18, least 19, at least 20, at least 25, at least 30, at least 35, at least 40, or at least 50 nucleotides in length. In some embodiments, the recognition sequence may be no more than 48, no more than 40, no more than 32, no more than 24, no more than 16, no more than 12, no more than 10, no more than 8, or no more than 6 nucleotides in length. Combinations of any of these are also possible, e.g., the recognition sequence may have a length of between 5 and 8, between 6 and 12, or between 7 and 15 nucleotides, etc. In some embodiments, the recognition sequence is of the same length as a barcode sequence or complement thereof of a primary nucleic acid probe or a product thereof. In some embodiments, the recognition sequence may be at least 50%, at least 60%, at least 70%, at least 75%, at least 80%, at least 85%, at least 90%, at least 92%, at least 94%, at least 95%, at least 96%, at least 97%, at least 98%, at least 99%, or at least 100% complementary to the barcode sequence or complement thereof.

In some embodiments, a nucleic acid probe, such as a primary or a secondary nucleic acid probe, may also comprise 1, 2, 3, 4, 5, 6, 7, 8, 9, 10, 11, 12, 13, 14, 15 or more, 20 or more, 32 or more, 40 or more, or 50 or more barcode sequences. As an illustrative example, a first probe may contain a first target-binding sequence, a first barcode sequence, and a second barcode sequence, while a second, different probe may contain a second target-binding sequence (that is different from the first target-binding sequence in the first probe), the same first barcode sequence as in the first probe, but a third barcode sequence instead of the second barcode sequence. Such probes may thereby be distinguished by determining the various barcode sequence combinations present or associated with a given probe at a given location in a sample.

In some embodiments, the nucleic acid probes disclosed herein may be made using only 2 or only 3 of the 4 bases, such as leaving out all the "G"s and/or leaving out all of the "C"s within the probe. Sequences lacking either "G"s or "C"s may form very little secondary structure, and can contribute to more uniform, faster hybridization in certain embodiments.

In some embodiments, a nucleic acid probe disclosed herein may contain a detectable label such as a fluorophore. In some embodiments, one or more probes of a plurality of nucleic acid probes used in an assay may lack a detectable label, while one or more other probes in the plurality each comprises a detectable label selected from a limited pool of distinct detectable labels (e.g., red, green, yellow, and blue fluorophores), and the absence of detectable label may be used as a separate "color." As such, detectable labels are not required in all cases. In some embodiments, a primary nucleic acid probe disclosed herein lacks a detectable label. While a detectable label may be incorporated into an amplification product of a probe, such as via incorporation of a modified nucleotide into an RCA product of a circularized probe, the amplification product itself in some embodiments is not detectably labeled. In some embodiments, a probe that binds to the primary nucleic acid probe or a product thereof (e.g., a secondary nucleic acid probe that binds to a barcode sequence or complement thereof in the primary nucleic acid probe or product thereof) comprises a detectable label and may be used to detect the primary nucleic acid probe or product thereof. In some embodiments, a secondary nucleic acid probe disclosed herein lacks a detectable label, and a detectably labeled probe that binds to the secondary nucleic acid probe or a product thereof (e.g., at a barcode sequence or complement thereof in the secondary nucleic acid probe or product thereof) can be used to detect the second nucleic acid probe or product thereof. In some embodiments, signals associated with the detectably labeled probes (e.g., the first detectable probe which is detectably labelled, the second detectable probe which is detectably labelled, a detectably labeled probe that binds to the first detectable probe which itself is not detectably labelled, or a detectably labeled probe that binds to the second detectable probe which itself is not detectably labelled) can be used to detect one or more barcode sequences in the secondary probe and/or one or more barcode sequences in the primary probe, e.g., by using sequential hybridization of detectably labeled probes (e.g., smFISH-based detection), sequencing-by-ligation, and/or sequencing-by-hybridization. In some embodiments, the barcode sequences (e.g., in the secondary probe and/or in the primary probe) are used to combinatorially encode a plurality of analytes of interest. As such, signals associated with the detectably labeled probes at particular locations in a biological sample can be used to generate distinct signal signatures that each corresponds to an analyte in the sample, thereby identifying the analytes at the particular locations, e.g., for in situ spatial analysis of the sample.

In some embodiments, a nucleic acid probe herein comprises one or more other components, such as one or more primer binding sequences (e.g., to allow for enzymatic amplification of probes), enzyme recognition sequences (e.g., for endonuclease cleavage), or the like. The components of the nucleic acid probe may be arranged in any suitable order.

In some aspects, analytes are targeted by primary probes, which are barcoded through the incorporation of one or more barcode sequences (e.g., sequences that can be detected or otherwise "read") that are separate from a sequence in a primary probe that directly or indirectly binds the targeted analyte. In some aspects, the primary probes are in turn targeted by secondary probes, which are also barcoded through the incorporation of one or more barcode sequences that are separate from a recognition sequence in a secondary probe that directly or indirectly binds a primary probe or a product thereof. In some embodiments, a secondary probe may bind to a barcode sequence in the primary probe. In some aspects, tertiary probes and optionally even higher order probes may be used to target the secondary probes, e.g., at a barcode sequence or complement thereof in a secondary probe or product thereof. In some embodiments, the tertiary probes and/or even higher order probes may comprise one or more barcode sequences and/or one or more detectable labels. In some embodiments, a tertiary probe is a detectably labeled probe that hybridizes to a barcode sequence (or complement thereof) of a secondary probe (or product thereof). In some embodiments, through the detection of signals associated with detectably labeled probes in a sample, the location of one or more analytes in the sample and the identity of the analyte(s) can be determined. In some embodiments, the presence/absence, absolute or relative abundance, an amount, a level, a concentration, an activity, and/or a relation with another analyte of a particular analyte can be analyzed in situ in the sample.

In some embodiments, provided herein are probes, probe sets, and assay methods to couple target nucleic acid detection, signal amplification (e.g., through nucleic acid amplification such as RCA, and/or hybridization of a plurality of detectably labeled probes, such as in hybridization chain reactions and the like), and decoding of the barcodes.

In some aspects, a primary probe, a secondary probe, and/or a higher order probe can be selected from the group consisting of a circular probe, a circularizable probe, and a linear probe. In some embodiments, a circular probe can be one that is pre-circularized prior to hybridization to a target nucleic acid and/or one or more other probes. In some embodiments, a circularizable probe can be one that can be circularized upon hybridization to a target nucleic acid and/or one or more other probes such as a splint. In some embodiments, a linear probe can be one that comprises a target recognition sequence and a sequence that does not hybridize to a target nucleic acid, such as a 5' overhang, a 3' overhang, and/or a linker or spacer (which may comprise a nucleic acid sequence or a non-nucleic acid moiety). In some embodiments, the sequence (e.g., the 5' overhang, 3' overhang, and/or linker or spacer) is non-hybridizing to the target nucleic acid but may hybridize to one another and/or one or more other probes, such as detectably labeled probes.

Specific probe designs can vary depending on the application. For instance, a primary probe, a secondary probe, and/or a higher order probe disclosed herein can comprise a circularizable probe that does not require gap filling to circularize upon hybridization to a template (e.g., a target nucleic acid and/or a probe such as a splint), a gapped circularizable probe (e.g., one that requires gap filling to circularize upon hybridization to a template), an L-shaped probe (e.g., one that comprises a target recognition sequence and a 5' or 3' overhang upon hybridization to a target nucleic acid or a probe), a U-shaped probe (e.g., one that comprises a target recognition sequence, a 5' overhang, and a 3' overhang upon hybridization to a target nucleic acid or a probe), a V-shaped probe (e.g., one that comprises at least two target recognition sequences and a linker or spacer between the target recognition sequences upon hybridization to a target nucleic acid or a probe), a probe or probe set for proximity ligation (such as those described in U.S. Pat. Nos. 7,914,987 and 8,580,504 incorporated herein by reference in their entireties, and probes for Proximity Ligation Assay (PLA) for the simultaneous detection and quantification of nucleic acid molecules and protein-protein interactions), or any suitable combination thereof. In some embodiments, a primary probe, a secondary probe, and/or a higher order probe disclosed herein can comprise a probe that is ligated to itself or another probe using DNA-templated and/or RNA-templated ligation. In some embodiments, a primary probe, a secondary probe, and/or a higher order probe disclosed herein can be a DNA molecule and can comprise one or more other types of nucleotides, modified nucleotides, and/or nucleotide analogues, such as one or more ribonucleotides. In some embodiments, the ligation can be a DNA ligation on a DNA template. In some embodiments, the ligation can be a DNA ligation on an RNA template, and the probes can comprise RNA-templated ligation probes. In some embodiments, a primary probe, a secondary probe, and/or a higher order probe disclosed herein can comprise a padlock-like probe or probe set, such as one described in US 2019/0055594, US 2021/0164039, US 2016/0108458, or US 2020/0224243, each of which is incorporated herein by reference in its entirety. Any suitable combination of the probe designs described herein can be used.

In some embodiments, a probe disclosed herein can comprise two or more parts. In some cases, a probe can comprise one or more features of and/or be modified based on: a split FISH probe or probe set described in WO 2021/167526A1 or Goh et al., "Highly specific multiplexed RNA imaging in tissues with split-FISH," Nat Methods 17(7):689-693 (2020), which are incorporated herein by reference in their entireties; a Z-probe or probe set, such as one described in U.S. Pat. No. 7,709,198 B2, U.S. Pat. No. 8,604,182 B2, U.S. Pat. No. 8,951,726 B2, U.S. Pat. No. 8,658,361 B2, or Tripathi et al., "Z Probe, An Efficient Tool for Characterizing Long Non-Coding RNA in FFPE Tissues," Noncoding RNA 4(3):20 (2018), which are incorporated herein by reference in their entireties; an HCR initiator or amplifier, such as one described in U.S. Pat. No. 7,632,641 B2, US 2017/0009278 A1, U.S. Pat. No. 10,450,599 B2, Dirks and Pierce, "Triggered amplification by hybridization chain reaction," PNAS 101(43):15275-15278 (2004), Chemeris et al., "Real-time hybridization chain reaction," Dokl. Biochem 419:53-55 (2008), Niu et al., "Fluorescence detection for DNA using hybridization chain reaction with enzyme-amplification," Chem Commun (Camb) 46(18): 3089-91 (2010), Choi et al., "Programmable in situ amplification for multiplexed imaging of mRNA expression," Nat Biotechnol 28(11):1208-12 (2010), Song et al., "Hybridization chain reaction-based aptameric system for the highly selective and sensitive detection of protein," Analyst 137 (6):1396-401 (2012), Choi et al., "Third-generation in situ hybridization chain reaction: multiplexed, quantitative, sensitive, versatile, robust," Development 145(12): dev165753 (2018), or Tsuneoka and Funato, "Modified in situ Hybridization Chain Reaction Using Short Hairpin DNAs," Front Mol Neurosci 13:75 (2020), which are incorporated herein by reference in their entireties; a PLAYR probe or probe set, such as one described in US 2016/0108458 A1 or Frei et al., "Highly multiplexed simultaneous detection of RNAs and proteins in single cells," Nat Methods 13(3):269-75 (2016), which are incorporated herein by reference in their entireties; a PLISH probe or probe set, such as one described in US 2020/0224243 A1 or Nagendran et al., "Automated cell-type classification in intact tissues by single-cell molecular profiling," eLife 7:e30510 (2018), which are incorporated herein by reference in their entireties; a RollFISH probe or probe set such as one described in Wu et al., "RollFISH achieves robust quantification of single-molecule RNA biomarkers in paraffin-embedded tumor tissue samples," Commun Biol 1, 209 (2018), which is hereby incorporated by reference in its entirety; a MERFISH probe or probe set, such as one described in WO 2020/123742 A1 (PCT/US2019/065857) or Chen et al., "Spatially resolved, highly multiplexed RNA profiling in single cells," Science 348(6233):aaa6090 (2015), which are incorporated herein by reference in their entireties; or a primer exchange reaction (PER) probe or probe set, such as one described in US 2019/0106733 A1, which is hereby incorporated by reference in its entirety.

A. Detectably-Labeled Probes

In some embodiments, probes disclosed herein comprise a detectable moiety, a quencher moiety, and a hybridization sequence designed to hybridize to a sequence on a target nucleic acid or a sequence on a hybridized probe of a previous cycle (e.g., the probe hybridized and imaged in the most recent cycle). Methods for binding and identifying a target nucleic acid that uses various probes or oligonucleotides have been described in, e.g., US2003/0013091, US2007/0166708, US2010/0015607, US2010/0261026, US2010/0262374, US2010/0112710, US2010/0047924, and US2014/0371088, each of which is incorporated herein by reference in its entirety. Detectably-labeled probes can be useful for detecting multiple target nucleic acids and be detected in one or more hybridization cycles (e.g., sequential hybridization in a FISH-type assay, sequencing by hybridization).

In some embodiments, the assays described herein include the use of one or more probes that are directly or indirectly labeled. In some embodiments, the probe can form a secondary structure (e.g., a hairpin structure), similarly to the structure of molecular beacons. However, in other embodiments, the probe does not form a secondary structure, and is a linear, single stranded probe prior to hybridization to its target sequence. Unlike molecular beacon probes, the target of the quencher moiety is not the detectable moiety located on the same probe, but rather the detectable moiety of a previously hybridized and/or previously imaged probe. Thus, while the detectable signal of the probe can be quenched prior to hybridization of the probe, in some embodiments, the quencher does not quench the detectable moiety on the same probe either before or after hybridization. In some embodiments, the absorption spectrum of the quencher and the emission spectrum of the detectable moiety on the same probe do not overlap or have minimal overlap, such that the quencher does not quench the detectable moiety on the same probe.

The ability of the quencher moiety to specifically quench the detectable signal of the previously hybridized probe (e.g., a probe that has already been detected) without quenching the signal of the detectable moiety of the same probe allows detection of a second detectable moiety without detection of a first detectable moiety, although the first detectable moiety can remain in the sample. In some embodiments, the detectable moiety D1 of a first probe remains in the biological sample during and/or after a second contacting step and detection of the second detectable moiety. In some embodiments, D1 remains in the biological sample prior to, during, and/or after the detection of the detectable signal from D2. In some embodiments, D1 remains in the first probe during and/or after the second contacting step. In some embodiments, D1 remains in the first probe prior to, during, and/or after the detection of the detectable signal from D2. In some embodiments, the detectable signal from D2 is detected prior to, during, and/or after hybridization of H2 to H2'. In some embodiments, the detectable signal from D1 is detected prior to hybridization of H2 to H2'. In some embodiments, upon hybridization of H2 to H2', the detectable signal from D1 is not detected while the detectable signal from D2 is detected.

In some embodiments, the separation between the quencher and the detectable moiety on the same probe is sufficient to prevent quenching of the detectable moiety by the quencher on the same probe. In some embodiments, the separation between the quencher and the detectable moiety can be established after the probe is bound to its target sequence. In some embodiments, the quencher and detectable moiety of a probe are separated by at least 5 nucleotides up to about 50 nucleotides (e.g., by about 10-20 nucleotides, about 20-30 nucleotides, about 30-40 nucleotides, or about 40-50 nucleotides). In some embodiments, quenching occurs within a distance of less than 30-40 angstroms from the quencher. In some embodiments, the quencher and detectable moiety of a probe are separated by at least 7 nucleotides. In some embodiments, the quencher and the detectable moiety are separated by more than 50 nucleotides, e.g., 50-60 nucleotides, 60-70 nucleotides, 70-80 nucleotides, 80-90 nucleotides, or 90-100 nucleotides. In some embodiments, the first probe and/or the second probe are between about 10 and about 100 nucleotides in length, e.g., between about 15 and about 50 nucleotides in length.

In some embodiments, D1 is at the 3' end of the first probe, Q1 is at the 5' end of the second probe, and D2 is at the 3' end of the second probe. In some embodiments, D1 is at the 5' end of the first probe, Q1 is at the 3' end of the second probe, and D2 is at the 5' end of the second probe.

Figure 4:
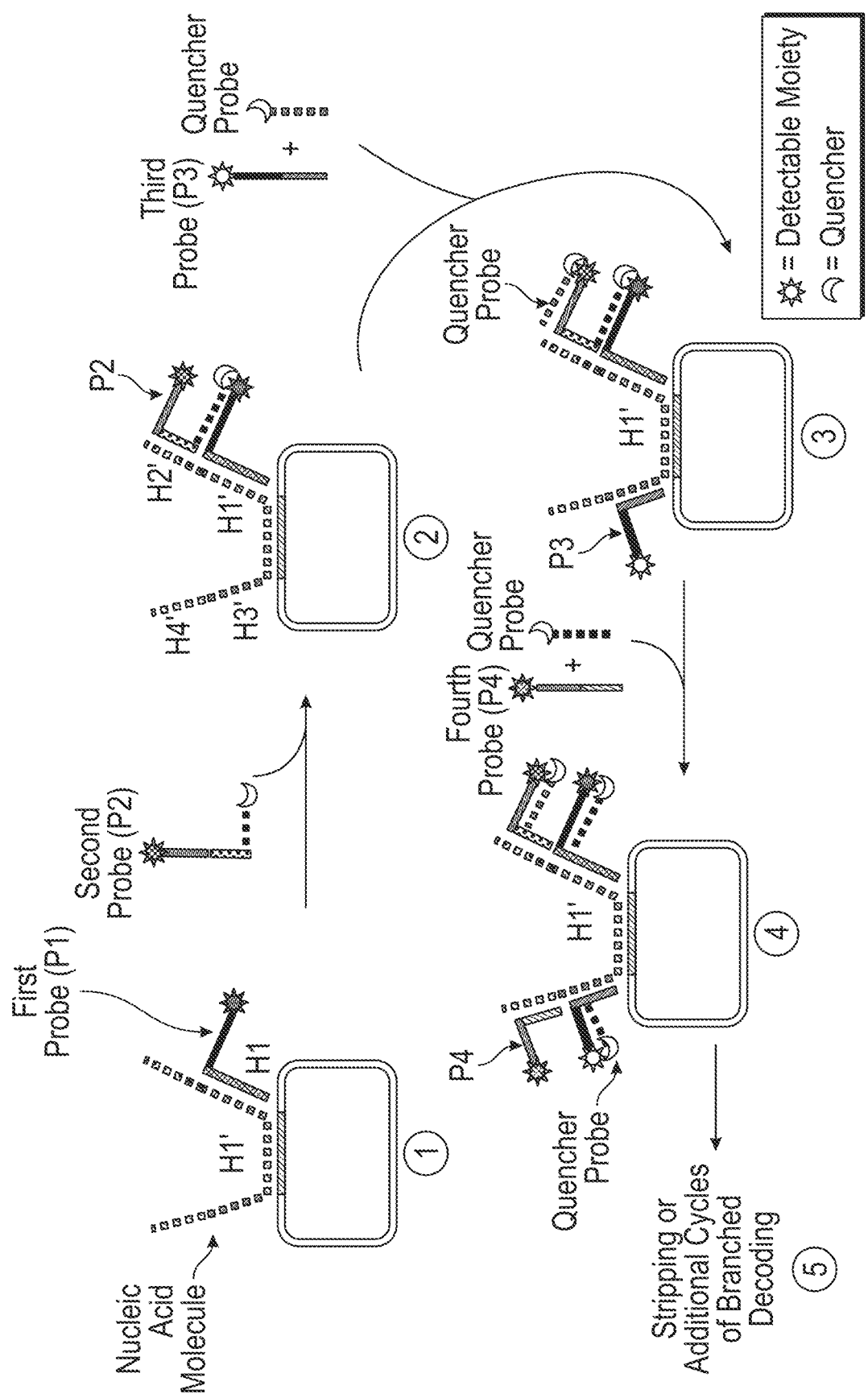
FIG. 4 shows an example where the quencher and the detectable moiety may be in the same probe molecule (e.g., P2 in contacting step 2) or in separate probe molecules (e.g., P3 and quencher probe in contacting step 3). The nucleic acid molecule may be a probe comprising an overhang on both the 5' and the 3' upon binding to another molecule, such as upon hybridization to a genomic DNA, coding or non-coding RNA (e.g., mRNA), cDNA, another probe, or a rolling circle amplification (RCA) product. In some examples, the nucleic acid molecule may be a detectable probe that hybridizes to a barcode region or complement thereof, e.g., in a probe or in an RCA product.
Figure 5:
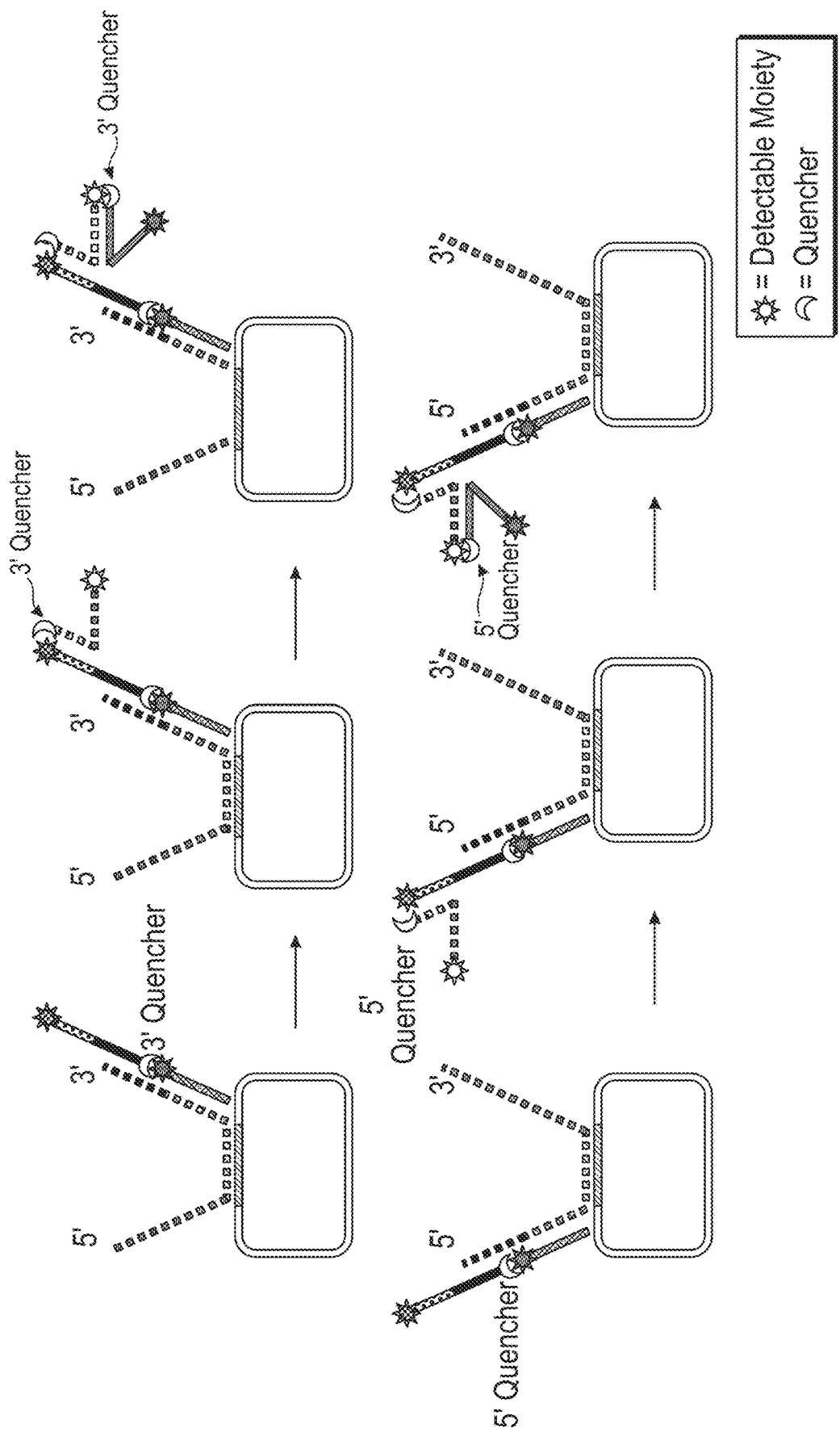
FIG. 5 shows exemplary embodiments of the method wherein the quencher is conjugated to the 3' end of the probe (top panel) or to the 5' end of the probe (bottom panel).
Figure 6:
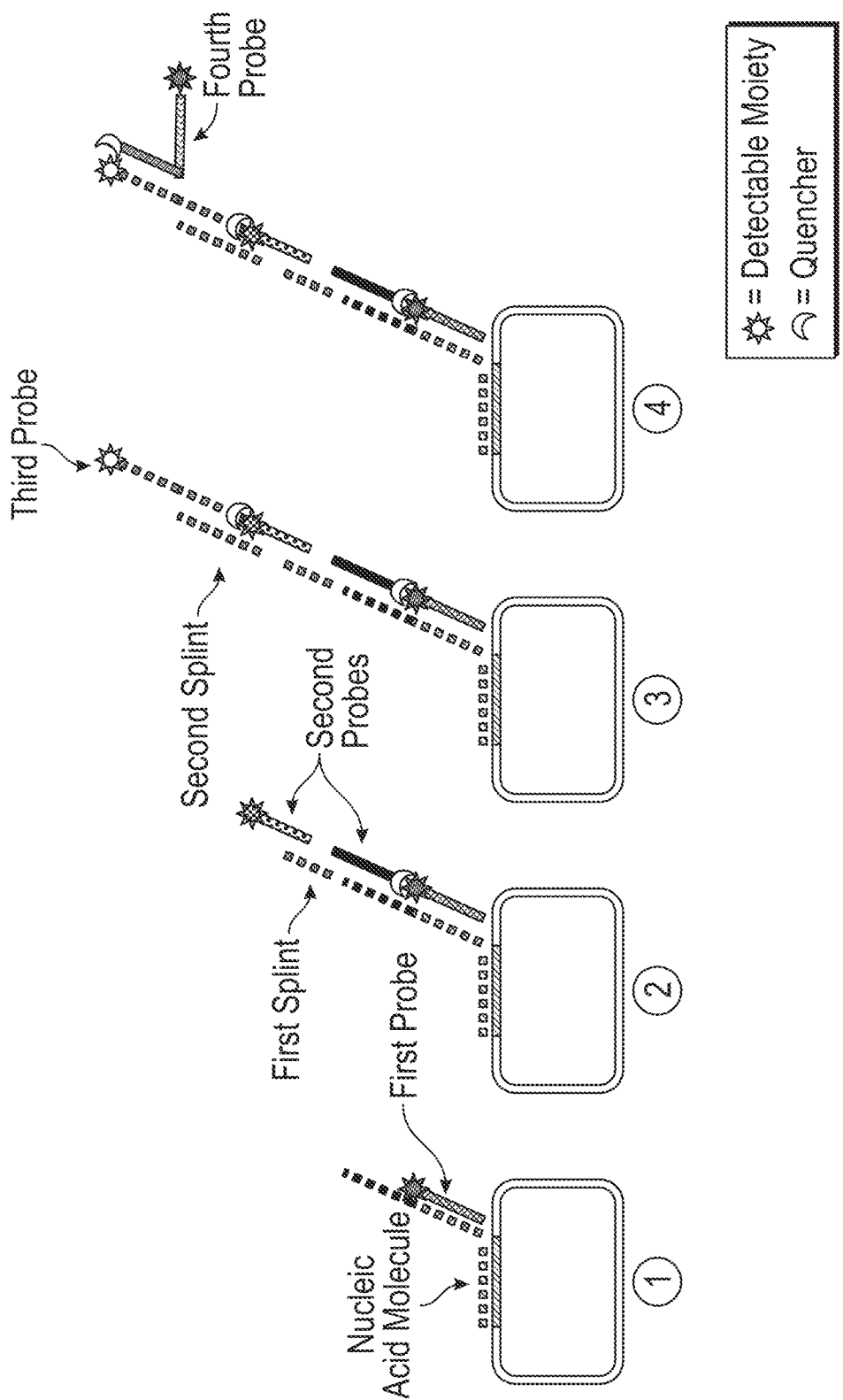
FIG. 6 shows an example where the quencher and the detectable moiety can be in different probe molecules connected by a splint (e.g., the first splint hybridizes to the two second probes in contacting step 2), and the detectable moiety of a probe in one cycle can be brought in proximity to the quencher of a probe in the next cycle by a splint (e.g., the second splint hybridizes to the third probe and one of the second probes in contacting step 3). The use of splints can be combined with any of the probe designs shown in FIGS. 1-5.

In some embodiments, a probe is a single oligonucleotide comprising both a quencher moiety and a detectable moiety. In some embodiments, the probe can comprise multiple separate oligonucleotide molecules that can be associated with one another, e.g., via a splint (e.g., as shown in FIG. 6). For example, the splint may comprise a first region that hybridizes to the oligonucleotide comprising the quencher moiety and a second region that hybridizes to the oligonucleotide comprising the detectable moiety. In some instances, the detectable moiety and the quencher moiety are conjugated to separate oligonucleotides (e.g., a quencher oligonucleotide probe and a detectable oligonucleotide probe). As shown in FIG. 4, the quencher oligonucleotide probe can hybridize to a sequence in the target nucleic acid and/or a probe of a previous contacting step such that it is in proximity to the detectable moiety of the previous contacting step, thereby quenching the detectable moiety of the previous contacting step. The detectable oligonucleotide probe can hybridize to a sequence of the target nucleic acid and/or a probe of a previous contacting step such that it is not quenched by the quencher. In some embodiments, the detectable oligonucleotide probe provides a hybridization sequence (e.g., an overhang sequence) for hybridization of probes added in future contacting steps.

B. Quenchers

In some embodiments, the methods herein comprise sequence-directed quenching of the detectable moiety of a previously hybridized probe by a quencher conjugated to the next probe (e.g., quenching a first detectable moiety D1 using a quencher Q1 conjugated to a second probe, wherein the second probe comprises a second detectable moiety D2). In some embodiments, a quencher moiety is brought into proximity with a detectable moiety of a bound probe (e.g., first probe) by hybridization of a subsequent probe (e.g., second probe) comprising the quencher moiety, thereby specifically quenching the signal from the detectable moiety of the previously bound probe. In some embodiments, the signal from the detectable moiety of a previously bound probe is detected or observed prior to contacting the sample with a subsequent probe comprising the quencher moiety. In some embodiments, the quencher is a non-fluorescent quencher. Non-fluorescent quenchers have been described, for example, in U.S. Pat. No. 7,879,986 and in U.S. Pat. No. 7,019,129, the contents of which are herein incorporated by reference in their entirety. Commonly used non-fluorescent quenchers include DABCYL, TAMRA, BlackHole Quenchers™ (BHQ, e.g. BHQ, BHQ1, or BHQ2), Biosearch Technologies, Inc. (Novato, Cal.), Iowa Black™, Integrated DNA Tech., Inc. (Coralville, Iowa), BlackBerry™ Quencher 650 (BBQ-650), Berry & Assoc., (Dexter, Mich.).

In some embodiments, Q1 is brought into proximity with D1 by hybridization of the second probe, thereby specifically quenching the signal from D1. In some embodiments, Q1 is not in sufficient proximity to D2 upon hybridization the second probe to allow for quenching of D2. In some embodiments, the quencher and detectable moiety of a given probe (e.g., Q1 and D2) are separated by at least 5 nucleotides up to about 50 nucleotides. In some embodiments, D1 is at the 3' end of the first probe, Q1 is at the 5' end of the second probe, and D2 is at the 3' end of the second probe. In some embodiments, D1 is at the 5' end of the first probe, Q1 is at the 3' end of the second probe, and D2 is at the 5' end of the second probe. In some embodiments, D1 remains in the biological sample and the detectable signal from D1 is not detected in step b). In some embodiments, the detectable signal from D1 is detected prior to step b).

In some embodiments, the quencher moiety to quench a first probe is added at the same time as the second probe comprising a second detectable moiety. The quencher and the detectable moiety can be on the same molecule (e.g., on either end of a single probe) or on separate oligonucleotide molecules. In some embodiments, hybridization of the quencher and/or the probe comprising the detectable moiety to their corresponding hybridization sequences in the nucleic acid and/or the first probe directs specific quenching of the first detectable moiety, while the second detectable moiety is not quenched. In some embodiments, the absorption spectrum of a quencher moiety and the emission spectrum of a detectable moiety on the second probe do not overlap.

The sequence use of sequence-directed quenching obviates the need for a separate signal removal step (e.g., deactivating or quenching the signal of the first probe) prior to the addition of the second probe. Thus, in some embodiments, there is no need for a separate signal removal step. For example, the methods provided herein do not require a separate signal removal step according to any of the signal removal methods known in the art, such as photobleaching, chemical deactivation, chemical cleavage of the fluorophores (e.g., disulfide cleavage), enzymatic cleavage (using, for example, an exonuclease, endonuclease, protease, or USER™ (Uracil-Specific Excision Reagent) cleavage system), DNA/RNA strand displacement, chemical or heat denaturing of an intermediate fluorescent oligonucleotide, and the like.

By eliminating a separate removal step, the methods provided herein can provide a more efficient method for analyzing multiple target analytes in a sample. Methods such as photobleaching are time-consuming. Alternatives such as chemical deactivation or chemical or enzymatic cleavage of detectable moieties from decoding probes are also time consuming (e.g., requiring a 30 minute removal step per cycle for chemically cleavable fluorophores).

Furthermore, the sequence-directed quenching reduces the number of washes needed, as the quenchers and detectable moieties hybridized to the sample in previous cycles can remain bound to the sample in subsequent contacting and detection cycles.

C. Detection and Analysis

In some aspects, provided herein is a method for detecting the detectably-labelled probes described in Section III.A, thereby generating a signal signature. In some cases, the signals for a given cycle is detectable and allowed by the quencher which can remove signals from a previous cycle. In some embodiments, the signal signature corresponds to an analyte of a plurality of analytes, as described in Section II. In some embodiments, the methods described herein are based, in part, on the development of a multiplexed biological assay and readout, in which a sample is first contacted with a plurality of nucleic acid molecules comprising one or more probe types (e.g., labelling agent, padlock probe, circular probe, etc.), allowing the probes to directly or indirectly bind target analytes, which may then be optically detected (e.g., by detectably-labelled probes) in a temporally-sequential manner (e.g., as shown in Table 1).

TABLE 1

Exemplary signals from m detection cycles

|  | Cycle 1 | Cycle 2 | ... Cycle m |
|---|---|---|---|
| Nucleic acid 1 | G | G(Q), Y | ... G(Q), Y(Q), ..., R |
| Nucleic acid 2 | Y | Y(Q), R | ... Y(Q), R(Q), ..., G |
| Nucleic acid 3 | R | R(Q), G | ... R(Q), G(Q), ..., Y |

In some aspects, an assay may comprise a series of probe hybridizations and probe detection with quenching of the previously hybridized probe wherein this cycle is repeated two or more times in order to generate a unique signal signature. As an exemplary assay shown in Table 1, the presence of a quenched detectable moieties of previous hybridization cycles is indicated as X(Q), wherein X is the detectable moiety (e.g., a green (G), red (R), yellow (Y), or blue (B) fluorescent moiety) and (Q) indicates that the detectable moiety is quenched. In some embodiments, each signal signature corresponds to a target analyte (e.g., nucleic acid molecules) in a sample. In some embodiments, the signal signature after m cycles comprises a sequence of observed signals.

In one aspect, the methods provided herein involve detecting a plurality of analytes in a sample, as described in Section II. In some embodiments, the method presented herein comprises: (a) contacting the sample with a plurality of labelling agents (e.g., padlock probes, circular probes, reporter oligonucleotides) as described herein, wherein each subpopulation of the labelling agents may target at least one different analyte; and (b) detecting in a temporally-sequential manner the plurality of the reporter oligonucleotides of the plurality labelling agents, wherein said detection of the reporter oligonucleotides each generates a signal signature corresponding to a barcode, and wherein a temporal order of the signal signature corresponding to said plurality of the reporter oligonucleotides of said labelling agent identifies a subpopulation of the labelling agents. In some embodiments, the temporal order of the signal signatures corresponding to said plurality of the reporter oligonucleotides of said labelling agent can be unique for each subpopulation of the labelling agent.

In some embodiments, the analysis and/or sequence determination involves washing to remove unbound polynucleotides (e.g., primary, secondary, or tertiary detectably-labelled probes), thereafter revealing a fluorescent product for imaging.

In some embodiments, the detection comprises imaging the sample or a region thereof in each of the detection steps. In some aspects, the imaging can be performed using any suitable means and systems. In some examples, the imaging is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detectably-labelled probes. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

The spatial movement limit of an analyte (or a product or derivative thereof) in a sample allowed for a temporal detection of the detectably-labelled probes to occur can vary depending on a number of factors, including, but not limited to, presence of any distinguishable features within a field of detection, magnification used in detection (e.g., magnification of the microscope lens), density of the analytes in a sample, and any combinations thereof. In some embodiments, there can be no limit in the spatial movement of an analyte in a sample during a temporal detection of the detection reagents, for example, provided that the analyte stay within the field of detection and there is at least one same distinguishable feature in each image taken during a temporal detection so that the images can be aligned to each other based on the same distinguishable feature. In some embodiments where there is no such distinguishable feature, the spatial movement of an analyte in a sample can be less than 100 µm, including less than 50 µm, less than 25 µm, less than 10 µm, less than 1 µm or smaller, over a time period, during which a temporal detection of the detection reagents occurs. In some embodiments, the spatial movement of an analyte in a sample can be less than 1000 nm, including less than 500 nm, less than 250 nm, less than 100 nm, less than 50 nm, less than 10 nm or smaller, over a time period, during which a temporal detection of the labelling agents occurs. More importantly, the spatial movement limit of an analyte in a sample during a temporal detection is determined by the ability of matching distinguishable features between images taken during a temporal detection, which can be affected by imaging conditions. In some embodiments, the analyte can be fixed on a solid substrate or support.

FIG. 1 shows exemplary embodiments of the methods provided herein. Each panel shows an exemplary hybridization complex formed after a first (1), a second (2), a third (3), and a fourth (4) contacting step. The biological sample can comprise a nucleic acid molecule comprising a hybridization sequence H1'. In (1), the sample is contacted with a first probe comprising a detectable moiety D1 (e.g., a red fluorophore) and a hybridization sequence H1, wherein H1' hybridizes to H1. In (2), the sample is contacted with a second probe, wherein the second probe comprises: (i) a hybridization sequence H2, (ii) a quencher Q1, and (iii) a detectable moiety (e.g., a green fluorophore) D2. The hybridization sequence H2 hybridizes to a sequence H2' of the nucleic acid and/or the first probe, wherein upon hybridization of H2 and H2', Q1 is in proximity to D1, thereby quenching a detectable signal from D1. Thus, a detectable signal can be detected from D2 without detecting D1 in (2), although the first probe and D1 can remain in the sample. In some embodiments, although quencher Q1 and detectable moiety D2 are in the same molecule (or linked together by a splint), Q1 does not quench D2.

Figure 2:
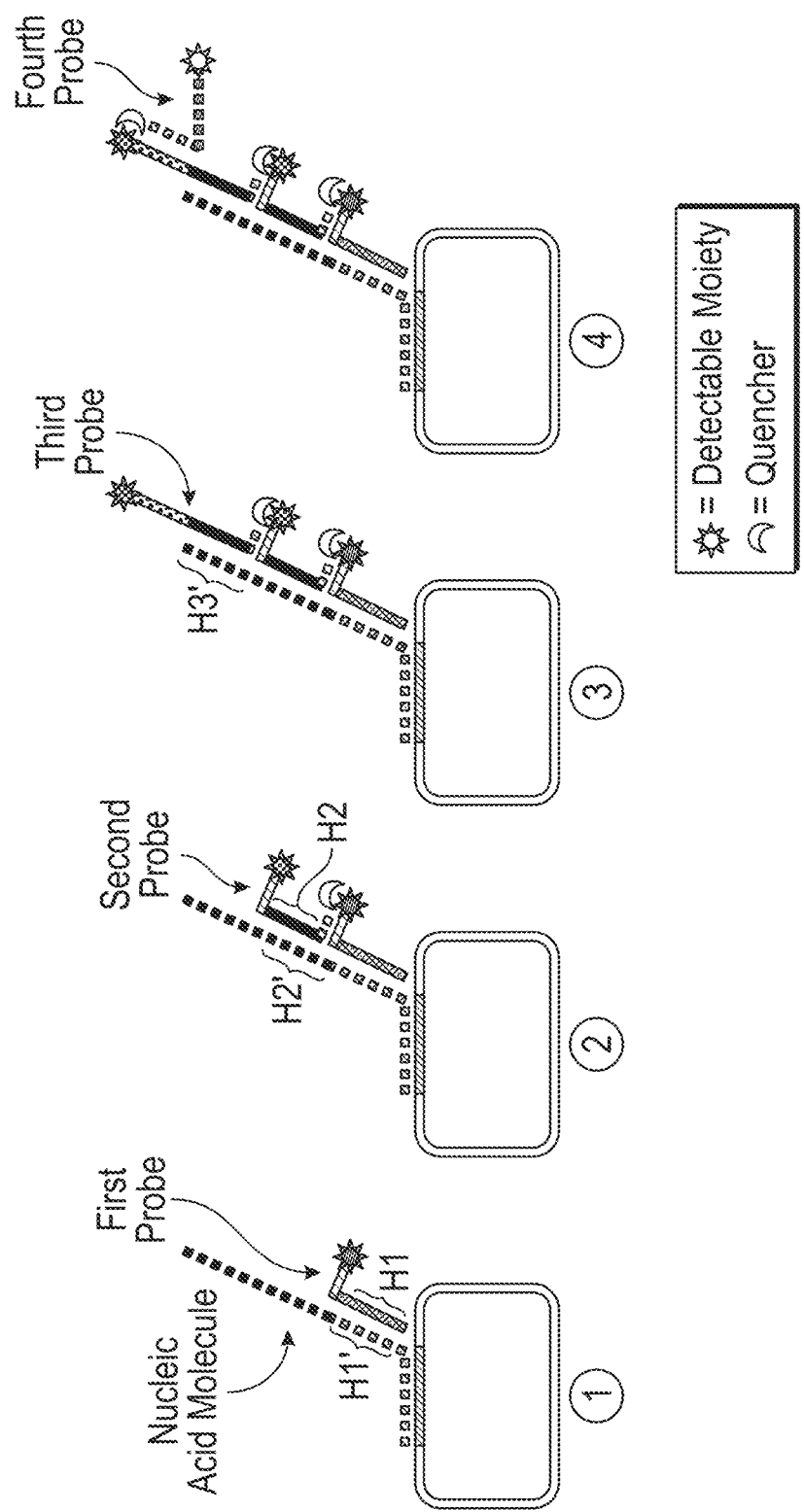
FIG. 2 shows exemplary hybridization complexes formed in a first (1), second (2), third (3), and fourth (4) contacting steps. The nucleic acid molecule comprises a landing sequence for hybridizing to the first, the second, and the third probes, and the third probe comprises a landing sequence for hybridizing to the fourth probe. The detectable moiety of a probe is quenched by a quencher of the next probe, eliminating the signal without physically removing the probe, cleaving the detectable moiety of the probe, and/or photobleaching.

The H2' hybridization sequence can be part of the nucleic acid molecule as shown in FIG. 1 and FIG. 2. In some embodiments the first probe can further comprise an additional target sequence for a subsequent probe. The contacting step can be repeated in (3) with a third probe comprising (i) a hybridization sequence H3', (ii) a quencher Q2, and (iii) a detectable moiety (e.g., a green fluorophore) D3. The hybridization sequence H3' hybridizes to a sequence H3 of the second probe, wherein upon hybridization of H3 and H3', Q2 is in proximity to D2, thereby quenching a detectable signal from D2. Thus, a detectable signal can be detected from D3 without detecting D1 and/or D2, although D1 and/or D2 can remain in the sample. The contacting step can similarly be repeated in (4), whereby a third quencher Q3 is hybridized in proximity to D3, thereby quenching a detectable signal from D3 and allowing detection of D4 without detecting D1, D2, and/or D3.

As will be readily appreciated by one of ordinary skill in the art, the contacting step using the probe designs provided herein or variations thereof can be repeated any number of times (e.g., repeated for m cycles, wherein m is an integer, e.g., 1, 2, 3, 4, 5, 6, 7, 8, 9, 10 or more times). In some embodiments, after m contacting cycles, the probes can be removed using conventional techniques (e.g., chemical stripping such as formamide stripping), and the process can be repeated with a new set of probes. In some embodiments, the methods provided herein reduce or eliminate the need for stripping probes between cycles for sequential decoding.

Figure 3:
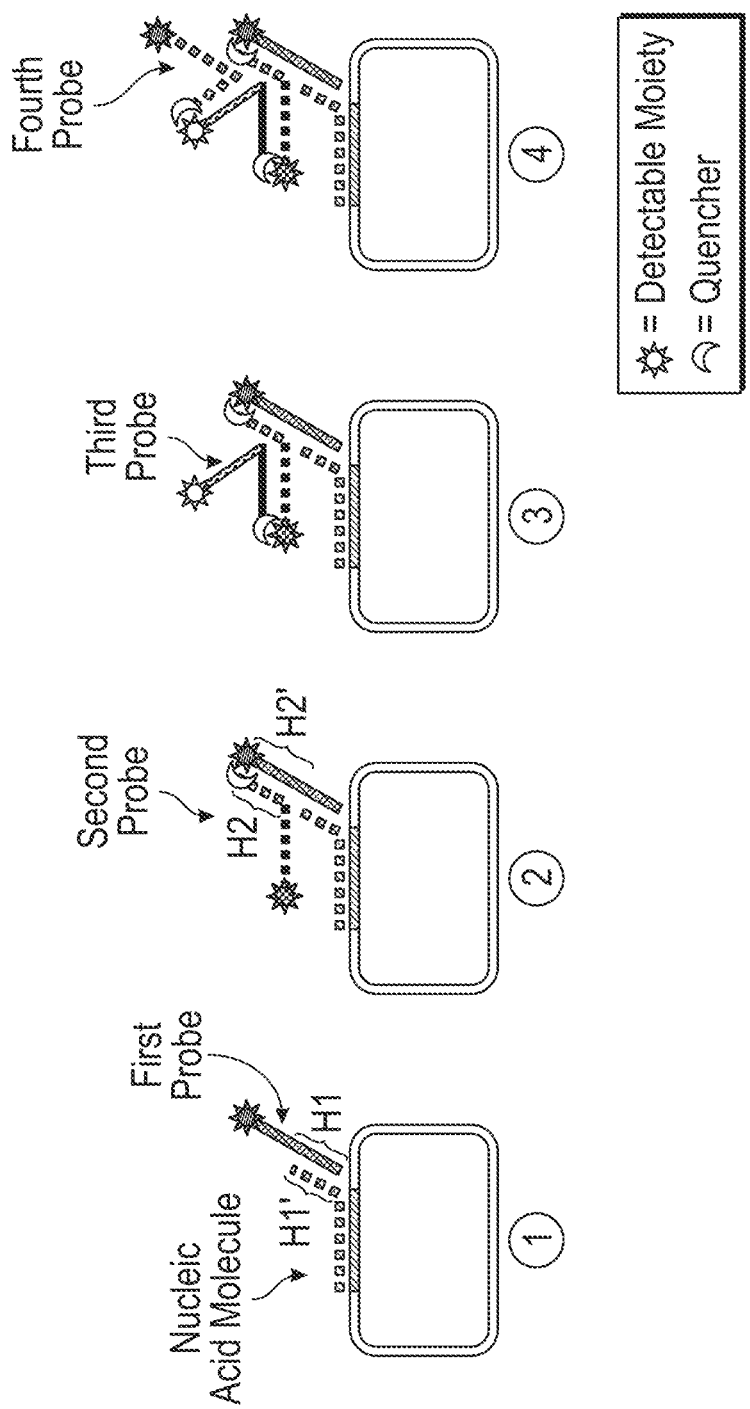
FIG. 3 shows exemplary hybridization complexes formed in a first (1), second (2), third (3), and fourth (4) contacting steps. The nucleic acid molecule comprises a landing sequence for hybridizing to the first probe, which comprise a landing sequence for hybridizing to the second probe, which in turn comprises a landing sequence for hybridizing to the third probe, which comprises a landing sequence for hybridizing to the fourth probe. The detectable moiety of a probe is quenched by a quencher of the next probe, eliminating the signal without physically removing the probe, cleaving the detectable moiety of the probe, and/or photobleaching.

Furthermore, as will be appreciated by one of ordinary skill in the art, variations of the hybridization design are possible that allow sequence specific hybridization-directed quenching of a detectable signal from a previously hybridized probe, as described in the methods provided herein. As shown in the top panel of FIG. 1, the nucleic acid can comprise an overhang region that extends beyond the first probe, and can comprise hybridization sequences for multiple probes (e.g., H1' and H2'). Similarly, the probes could comprise multiple hybridization sequences for subsequent probes, as shown in FIG. 2. As shown in FIG. 3, the first probe can comprise an overhang region that extends beyond the nucleic acid molecule, wherein the overhang region can comprise a hybridization sequence H2' for the second probe.

As shown in FIG. 4, in some embodiments, the nucleic acid molecule can be a U-probe, and the hybridization complex can comprise probes on both ends of the U-probe. In some embodiments, the probes can be designed as shown in FIGS. 1-3. In some embodiments, one or more of the probes comprising the quencher and the detectable moiety can comprise multiple oligonucleotide molecules, wherein the quencher Q is conjugated to a quencher probe and the detectable moiety is conjugated to a detection probe, as shown in FIG. 4, contacting step (3) and (4). For example, in step (2), the biological sample is contacted with probe P2, wherein: P2 comprises a detectable moiety D2, and a hybridization sequence H2, the biological sample comprises a nucleic acid molecule comprising a hybridization sequence H2', a hybridization sequence H3', and H2' hybridizes to H2. In cycle (3), the method comprises contacting the biological sample with probe P3 which comprises a detectable moiety D3 and a hybridization sequence H3 that hybridizes to H3'; and (ii) a quencher probe comprising a region HQ1 that hybridizes to a quencher target region HQ1' of P2, and upon hybridization of HQ1 and HQ1', the quencher is in proximity to D2, thereby quenching a detectable signal from D2, wherein a detectable signal from D3 is detected in the biological sample.

In some embodiments, the probes can be removed by conventional methods such as formamide stripping, or the branched decoding using quencher probes described above can be continued for any number of additional cycles by designing probes with additional hybridization sequences for subsequent probe annealing, such as using any one of the probe designs shown in FIGS. 1-4, as shown in step (5) of FIG. 4.

In some embodiments, quenching of the probe from the previous contacting step is directed by specific hybridization of the probe in the next cycle, such as any of the probes shown in FIGS. 1-4. In some embodiments, the quencher is conjugated to the 3' end of the probe, as shown in the top panel of FIG. 5. In some embodiments, the quencher is conjugated to the 5' end of the probe, as shown in the bottom panel of FIG. 5. In some embodiments, the probes are designed such that the quencher will be in proximity to the detectable moiety of the probe from the previous contacting step (e.g., the quencher is located at the end of the probe closest to the detectable moiety of the previous contacting step, as determined by the hybridization sequence of the probe).

In some embodiments, splints can be used to connect different probes of the hybridization complex as shown in FIG. 6. Splints can be used to connect probes in a linear or branched configuration. In some embodiments, the use of splints can be combined with any of the hybridization complex designs described above. In some embodiments, the splint can serve as a molecule that bridges two or more separate molecules via hybridization allowing a complex of three or more molecules to be formed. In some embodiments, a splint is an oligonucleotide that comprises a first region that hybridizes to at least a portion of a probe conjugated to a quencher moiety and a second region that hybridizes at least a portion of a probe conjugated to a detectable moiety. In some embodiments, the splint comprises a first region that hybridizes to at least a first probe comprising a detectable moiety and a second region that hybridizes at least a portion of a probe comprising both a detectable moiety and a quencher moiety. In some cases, the splint comprises a region that hybridizes to the probe Pm and a region that hybridizes to the probe P(m−1).

In some embodiments, the series of probe hybridizations and probe detection with quenching of the previously hybridized probe is repeated two or more times in order to generate a unique signal signature (Table 1). In some embodiments, the signal from each previously hybridized signal is quenched by the hybridization-directed quencher moiety of the subsequent probe, such that only the signal of the newly hybridized probe is detected in each cycle. The presence of quenched detectable moieties of previous hybridization rounds is indicated as X(Q), wherein X is the detectable moiety (e.g., a green, red, yellow, or blue fluorescent moiety) and (Q) indicates that the detectable moiety is quenched. In some embodiments, the probes can be removed (e.g., by stripping) after m cycles and the process can be repeated to generate a longer signal signature.

In some embodiments, each signal signature corresponds to a target analyte in a sample. In some embodiments, the number of analytes detected by the method is defined by the number of detectably-labeled probes and number of contacting steps (e.g., sequential hybridization of sets of detectably-labeled probes). In some embodiments, the method described herein is used for detecting about 3 to about 100,000 analytes within a sample, such as any of about 3 to about 1,000 analytes, about 500 to about 5,000 analytes, about 1,000 to about 50,000 analytes, or about 10,000 to about 100,000 analytes. In some embodiments, the method is used for detecting at least about 3 analytes, such as at least any of about 5, 10, 100, 1,000, 2,000, 3,000, 4,000, 5,000, 6,000, 7,000, 8,000, 9,000, 10,000, 50,000, or 100,000 analytes. In some embodiments, the method is used for detecting less than about 100,000 analytes, such as less than any of about 50,000, 10,000, 9,000, 8,000, 7,000, 6,000, 5,000, 4,000, 3,000, 2,000, 1,000, 100, 10, 5, or 3 analyte(s). In some embodiments, the method is used for detecting any of about 3, 5, 10, 100, 1,000, 2,000, 3,000, 4,000, 5,000, 6,000, 7,000, 8,000, 9,000, 10,000, 50,000, or 100,000 analytes.

IV. Compositions and Kits

In some aspects, provided herein are hybridization complexes generated according to any of the methods described herein. In some embodiments, provided herein is a hybridization complex comprising: (i) a nucleic acid molecule comprising a hybridization sequence H1', and H1' hybridizes to H1; (ii) a first probe comprising a detectable moiety D1 and a hybridization sequence H1, and (iii) a second probe comprising a hybridization sequence H2 that is hybridized to a hybridization region H2' of the nucleic acid molecule and/or hybridized to the first probe, a quencher Q1, and a detectable moiety D2, wherein the quencher Q1 is in proximity with the detectable moiety D1 of the hybridization complex, wherein a detectable signal from D2 can be detected from the hybridization complex. In some embodiments, the second probe is a single molecule. In some embodiments, the second probe comprises a quencher probe comprising the quencher Q1 and a detection probe comprising the detectable moiety D2, wherein the quencher probe and the detection probe are separate molecules. In some embodiments, the second probe further comprises a splint oligonucleotide that hybridizes to the quencher probe and the detection probe. In some embodiments, the quencher and detectable moiety of the second probe are separated by at least 5 nucleotides up to about 50 nucleotides.

In some embodiments, the hybridization complex further comprises a third probe, wherein the third probe comprises: a hybridization sequence H3 that is hybridized to a hybridization region H3' of the nucleic acid molecule or the second probe, a quencher Q2, and a detectable moiety D3, wherein the quencher Q2 is in proximity to D2 in the hybridization complex, wherein a detectable signal from D3 can be detected from the hybridization complex. In some instances, a hybridization complex of a plurality of probes comprising quenchers and detectable moieties is formed on a probe that directly hybridizes to an analyte (e.g., mRNA) in the biological sample.

Also provided herein are kits, for analyzing an analyte in a biological sample according to any of the methods described herein. In some embodiments, provided herein is a kit comprising one or more of the probes disclosed herein, including the first probe P1, the second probe P2, and one or more subsequent probes. In some embodiments, a set of probes are designed and provided for each target and the kit may comprise a plurality of sets of probes for a plurality of targets.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

V. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® QuickLoad® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™ ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™ ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(x) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also refer to an "epitope binding fragment" or "antibody fragment," which as used herein, generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')$_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay, a capture probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labeled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, C1-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO- PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/ YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLE

The following example is included for illustrative purposes only and is not intended to limit the scope of the present disclosure.

Example 1: Decoding Using Sequential Hybridization

This example describes a method of decoding a sequence in a target nucleic acid by sequential hybridization of detectably labeled probes, wherein each hybridization step of a number m cycles (wherein m is an integer greater than or equal to 2) provides for quenching of the previously imaged probe. In some examples, the quenching can happen in the same step as contacting the sample with the new detectably labeled probe to be imaged.

In some examples, the target nucleic acid sequences can be endogenous nucleic acids (e.g., probes can hybridize to different regions of an mRNA to generate a signal signature corresponding to each targeted mRNA). In some examples, the target nucleic acids can include one or more one or more barcode(s), e.g., at least two, three, four, five, six, seven, eight, nine, ten, or more barcodes. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In an example, the target nucleic acid for the probes described herein is an L-shaped or U-shaped probe that binds to a barcode sequence of an analyte (e.g., an RCP generated using a primary probe that hybridizes to an endogenous nucleic acid in a sample as template). In some cases, the target nucleic acid for the probes is a probe that binds to a barcode sequence of a probe directly bound to an analyte (e.g., an endogenous nucleic acid in the sample, such as an mRNA). In some embodiments, multiple primary probes are bound to the same analyte (e.g., 20-50 primary probes may be hybridized to an mRNA). In some embodiments, the L-shaped or U-shaped probe comprises a region that hybridizes to the barcode and at least one overhang region on the 5' and/or the 3' sides.

The biological sample can comprise, Nucleic acid 1, Nucleic acid 2, Nucleic acid 3, . . . , and so on, up to the coding capacity of the system as determined by the number of sequential hybridizations, the number of different detectable moieties, and the number of detection channels of the imaging device. In an example, Nucleic acid 1, Nucleic acid 2, Nucleic acid 3, etc. are L-shaped probes that bind to an RCP associated with an analyte.

The biological sample is contacted in a first cycle with a set of first probes, each targeting a region of the nucleic acids comprising a hybridization sequence H1-n' (e.g., H1-1' for Nucleic acid 1, H1-2' for Nucleic acid 2, H1-3' for Nucleic acid 3, and so on). In the first cycle (e.g., (1) as shown in FIG. 1) the set of first probes, each comprising a detectable fluorescent moiety and a hybridization sequence, is contacted with the sample under conditions that promote hybridization of the probes to the nucleic acids (e.g., H1-1 hybridizes to H1-1', H1-2 hybridizes to H1-2', H1-3 hybridizes to H1-3', and so on). An example of the resulting hybridization complex for a given nucleic acid target after a contacting step is shown in FIG. 1 cycle (1). The sample is imaged, and the color of the first fluorescent moiety at each nucleic acid position detected is recorded.

The sample is then contacted in a second cycle with a set of second probes, each comprising a detectable fluorescent moiety, a hybridization sequence H2-n, and a quencher moiety Q1. The hybridization sequence H2-n hybridizes to a sequence H2-n' of the nucleic acid and/or the first probe, wherein upon hybridization of H2-n and H2-n', Q1 of a hybridized second probe is in proximity to the fluorescent moiety of the corresponding first probe, thereby quenching the signal of the first probe. The sample is imaged, and the color of the second fluorescent moiety at each nucleic acid position is detected and recorded. Thus, the hybridization-directed quenching of the first fluorescent moiety without requiring its removal from the sample or chemical inactivation obviates the need for a separate removal step in order to detect a single signal at each position in subsequent cycles.

The sample can be contacted in any number of cycles, wherein each probe in the set of cycles hybridizes to an overhang region of the nucleic acid or of a probe of a previous cycle. Exemplary embodiments of hybridization complexes generated according to this method are shown in FIGS. 1-6. The cycles of contacting and imaging the set of nucleic acid targets can yield a unique signal signature for each nucleic acid target (e.g., Table 1).

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a biological sample, comprising:
   a) contacting a biological sample with a first probe, wherein:
      the first probe comprises a detectable moiety D1 and a hybridization sequence H1,
      the biological sample comprises a nucleic acid molecule comprising a hybridization sequence H1', and
      H1' hybridizes to H1; and
   b) contacting the biological sample with a second probe, wherein:
      the second probe comprises: (i) a hybridization sequence H2 that hybridizes to a hybridization region H2' of the nucleic acid molecule, the first probe, or a splint, (ii) a quencher Q1, and (iii) a detectable moiety D2, and
      upon hybridization of H2 and H2', Q1 is in proximity to D1, thereby quenching a detectable signal from D1,
      wherein a detectable signal from D2 is detected in the biological sample.

2. The method of claim 1, wherein D1 remains in the biological sample during and/or after the contacting step b).

3. The method of claim 1, wherein DI remains in the first probe during and/or after the contacting step b).

4. The method of claim 1, wherein the first probe remains hybridized to the nucleic acid molecule during and/or after the contacting step b).

5. The method of claim 1, wherein the first probe remains hybridized to the nucleic acid molecule prior to, during, and/or after the detection of the detectable signal from D2,
   wherein the method does not comprise removing the first probe or a portion thereof from the nucleic acid molecule by enzymatically cleaving, modifying, or degrading the first probe or portion thereof,
   wherein the method does not comprise inactivating the first probe or a portion thereof by removing or modifying the detectable moiety D1,
   wherein the method does not comprise cleaving a linker linking the detectable moiety D1 to the first probe,
   wherein the method does not comprise chemically or photochemically modifying the detectable moiety D1,
   wherein the method does not comprise bleaching the detectable moiety D1 by a chemical agent,
   wherein the method does not comprise photobleaching the detectable moiety D1,
   wherein the method does not comprise permanently and irreversibly extinguishing the detectable moiety D1, and/or
   wherein the first probe and/or the second probe is not self-quenching.

6. The method of claim 1, wherein Q1 is not in sufficient proximity to D2 upon hybridization of H2 to H2' to quench the signal of D2 prior to detection.

7. The method of claim 1, wherein upon hybridization of H2 to H2', the detectable signal from D1 is not detected while the detectable signal from D2 is detected.

8. The method of claim 1, wherein D1 is at the 3' end of the first probe, Q1 is at the 5' end of the second probe, and D2 is at the 3' end of the second probe, or wherein D1 is at the 5' end of the first probe, Q1 is at the 3' end of the second probe, and D2 is at the 5' end of the second probe.

9. The method of claim 1, wherein the method further comprises:
   c) contacting the biological sample with a third probe, wherein:
      the third probe comprises: (i) a hybridization sequence H3 that hybridizes to a hybridization sequence H3' of the nucleic acid molecule, the probe of the previous contacting step, or a splint, (ii) a quencher Q2, and (iii) a detectable moiety D3, and
      upon hybridization of H3 and H3', Q2 is in proximity to D2, thereby quenching the detectable signal from D2,
      wherein a detectable signal from D3 is detected in the biological sample.

10. The method of claim 9, wherein D1 and D2 remain in the biological sample and the detectable signals from D1 and D2 are not detected in step c).

11. The method of claim 1, wherein the first probe and/or second probe are single-stranded linear oligonucleotide probes and do not form hairpin structures.

12. The method of claim 1, wherein the quencher does not quench a detectable signal of the detectable moiety on the same probe.

13. The method of claim 1, wherein the first detectable moiety D1 is detected in the first contacting step and not detected in the second contacting step; the second detectable moiety D2 is detected in the second contacting step and not detected in the first contacting step.

14. The method of claim 1, wherein the nucleic acid molecule in the biological sample comprises one or more barcode sequences.

15. The method of claim 1, wherein the nucleic acid molecule in the biological sample is a probe that hybridizes to an mRNA molecule, a cDNA molecule, a labelling agent that directly or indirectly binds to an analyte in the biological sample, and/or a product, a replication product, a transcription/reverse transcription product, and/or an amplification product of the mRNA molecule, the cDNA molecule, or the labelling agent.

16. The method of claim 1, wherein the biological sample is a tissue sample.

17. A method for analyzing a biological sample, comprising:
   a) contacting a biological sample with a first probe, wherein:
      the first probe comprises a detectable moiety D1, and a hybridization sequence H1,
      the biological sample comprises a nucleic acid molecule comprising a hybridization sequence H1', a hybridization sequence H2',
      H1' hybridizes to H1; and
   b) contacting the biological sample with:
      (i) a second probe, wherein the second probe comprises a detectable moiety D2 and a hybridization sequence H2 that hybridizes to H2'; and
      (ii) a first quencher probe Q1, wherein the first quencher probe comprises a region HQ1 that hybridizes to a quencher target region HQ1' of the first nucleic acid, the first probe, or a splint oligonucleotide that hybridizes to the first probe, and
      upon hybridization of HQ1 and HQ1', Q1 is in proximity to D1, thereby quenching a detectable signal from D1,
      wherein a detectable signal from D2 is detected in the biological sample.

18. The method of claim 17, wherein the nucleic acid molecule further comprises a hybridization sequence H3', and a hybridization sequence H4'.

19. The method of claim 18, wherein the method further comprises contacting the biological sample with:
  (i) a third probe, wherein the third probe comprises a detectable moiety D3 and a hybridization sequence H3 that hybridizes to H3'; and
  (ii) a second quencher probe Q2, wherein the second quencher probe comprises a hybridization sequence HQ2 that hybridizes to HQ2'; and
  upon hybridization of HQ2 and HQ2', Q2 is in proximity to D2, thereby quenching a detectable signal from D2, wherein a detectable signal from D3 is detected in the biological sample.

20. The method of claim 19, wherein the method further comprises contacting the biological sample with:
  (i) a fourth probe, wherein the fourth probe comprises a detectable moiety D4 and a hybridization sequence H4 that hybridizes to H4'; and
  (ii) a second quencher probe Q3, wherein the second quencher probe comprises a hybridization sequence HQ3 that hybridizes to HQ3'; and
  upon hybridization of HQ3 and HQ3', Q3 is in proximity to D3, thereby quenching a detectable signal from D3, wherein a detectable signal from D4 is detected in the biological sample.

* * * * *